(12) United States Patent
Harbury et al.

(10) Patent No.: US 10,358,641 B2
(45) Date of Patent: Jul. 23, 2019

(54) MONOLITHS WITH ATTACHED RECOGNITION COMPOUNDS, ARRAYS THEREOF AND USES THEREOF

(71) Applicant: DICE Molecules SV LLC, Menlo Park, CA (US)

(72) Inventors: Pehr Harbury, Portola Valley, CA (US); Madan Paidhungat, San Francisco, CA (US); Robin Prince, San Francisco, CA (US)

(73) Assignee: DiCE Molecules SV, LLC, Redwood City, CA (US)

( * ) Notice: Subject to any disclaimer, the term of this patent is extended or adjusted under 35 U.S.C. 154(b) by 732 days.

(21) Appl. No.: 14/608,114

(22) Filed: Jan. 28, 2015

(65) Prior Publication Data

US 2015/0209753 A1 Jul. 30, 2015

Related U.S. Application Data

(60) Provisional application No. 61/932,747, filed on Jan. 28, 2014, provisional application No. 62/006,845, filed on Jun. 2, 2014.

(51) Int. Cl.
| | |
|---|---|
| *B01J 19/00* | (2006.01) |
| *C12N 15/10* | (2006.01) |
| *C40B 50/14* | (2006.01) |
| *C40B 50/16* | (2006.01) |
| *C40B 70/00* | (2006.01) |

(52) U.S. Cl.
CPC ...... *C12N 15/1068* (2013.01); *B01J 19/0046* (2013.01); *C12N 15/1065* (2013.01); *C12N 15/1093* (2013.01); *C40B 50/14* (2013.01); *B01J 2219/005* (2013.01); *B01J 2219/00315* (2013.01); *B01J 2219/00423* (2013.01); *B01J 2219/00509* (2013.01); *B01J 2219/00547* (2013.01); *B01J 2219/00572* (2013.01); *B01J 2219/00592* (2013.01); *B01J 2219/00596* (2013.01); *B01J 2219/00639* (2013.01); *B01J 2219/00641* (2013.01); *B01J 2219/00722* (2013.01); *C40B 50/16* (2013.01); *C40B 70/00* (2013.01)

(58) Field of Classification Search
None
See application file for complete search history.

(56) References Cited

U.S. PATENT DOCUMENTS

| | | | |
|---|---|---|---|
| 4,889,632 A | 12/1989 | Svec et al. | |
| 4,923,610 A | 5/1990 | Svec et al. | |
| 4,952,349 A | 8/1990 | Svec et al. | |
| 5,281,368 A | 1/1994 | Dias et al. | |
| 5,539,082 A | 7/1996 | Nielsen et al. | |
| 5,773,571 A | 6/1998 | Nielsen et al. | |
| 5,811,238 A | 9/1998 | Stemmer et al. | |
| 6,395,474 B1 | 5/2002 | Buchardt et al. | |
| 6,919,181 B2 | 7/2005 | Hargreaves | |
| 7,473,367 B2 | 1/2009 | Xie | |
| 7,479,472 B1 | 1/2009 | Harbury et al. | |
| 7,977,109 B2 | 7/2011 | Ritt et al. | |
| 8,101,744 B2 | 1/2012 | Birkner et al. | |
| 8,148,115 B2 | 4/2012 | Reed et al. | |
| 8,158,349 B2 | 4/2012 | Block et al. | |
| 8,217,094 B2 | 7/2012 | Hosoya et al. | |
| 8,394,492 B1 | 3/2013 | Leventis et al. | |
| 8,563,620 B2 | 10/2013 | Bouazaoui et al. | |
| 8,586,350 B2 | 11/2013 | Toujou et al. | |
| 8,603,833 B2 | 12/2013 | Malik et al. | |
| 2005/0095602 A1 | 5/2005 | West et al. | |
| 2006/0078983 A1* | 4/2006 | Lau | B01J 19/0046 435/287.1 |
| 2006/0099626 A1* | 5/2006 | Harbury | C12N 15/1068 435/6.12 |
| 2007/0012627 A1* | 1/2007 | Ivanov | B01J 20/26 210/656 |
| 2011/0240541 A1 | 10/2011 | Gu et al. | |
| 2012/0248033 A1 | 10/2012 | Mallet et al. | |
| 2012/0276576 A1 | 11/2012 | Haddad et al. | |
| 2015/0315569 A1 | 11/2015 | Weisinger et al. | |

FOREIGN PATENT DOCUMENTS

| | | |
|---|---|---|
| CN | 1268979 A | 10/2000 |
| CN | 1961013 A | 5/2007 |
| CN | 101400993 A | 4/2009 |
| CN | 103038247 A | 4/2013 |
| GB | 1123878 | 8/1966 |
| WO | WO 92/07882 | 5/1992 |
| WO | WO 2000/015778 | 3/2000 |
| WO | WO-0015778 A1 * 3/2000 ........... B01D 15/325 |

(Continued)

OTHER PUBLICATIONS

Weisinger, Rebecca M., et al. "Mesofluidic devices for DNA-programmed combinatorial chemistry." PloS one 7.3 (2012): e32299.*
Li thesis "Development of Biocompatible Polymer Monoliths for the Analysis of Proteins and Peptides" (Dec. 8, 2009).*
Pahlow et al. ( ChemPhysChem 14.15 (2013): 3600-3605). (Year: 2013).*
U.S. Appl. No. 61/932,747, filed Jan. 28, 2014, Harbury, et al.—related case.
U.S. Appl. No. 62/006,845, filed Jun. 2, 2014, Harbury, et al.—related case.
Alder, K. and Windemuth, E. Uber die dien-synthese mit allyl-verbindungen (zur kenntnis der dien-synthese, Vi.Mittell.). Aus d. Chem. Institut d. Universitat Koln: 1939-1957 (1938).

(Continued)

Primary Examiner — Tracy Vivlemore
Assistant Examiner — Sahana S Kaup
(74) Attorney, Agent, or Firm — Fenwick & West LLP

(57) ABSTRACT

Provided herein are monoliths with attached recognition compounds which selectively bind ligands, methods of preparing such monoliths, arrays thereof and uses thereof. For example, monoliths provide herein can be used in columns and arrays thereof.

24 Claims, 8 Drawing Sheets

(56) References Cited

FOREIGN PATENT DOCUMENTS

| WO | WO 2008/012064 | 1/2008 |
|---|---|---|
| WO | WO 2008/130186 | 10/2008 |
| WO | WO 2010/053443 A1 | 5/2010 |
| WO | WO 2011/073446 | 6/2011 |
| WO | WO 2011/154859 | 12/2011 |
| WO | WO 2012/004204 | 1/2012 |
| WO | PCT US2015/013382 | 8/2015 |

OTHER PUBLICATIONS

Andac, M. et al. Dye attached poly(hydroxyethyl methacrylate) cryogel for albumin depletion from human serum. Journ. Sep. Sci. 35(9): 1173-1182 (2012).

Arap, W., et al. Cancer treatment by targeted drug delivery to tumor vasculature in a mouse model. Science 279(5349): 377-380 (1998).

Arrua, R.D., et al. Macroporous monolithic polymers: preparation and applications. Materials 2(4): 2429-2466 (2009).

Arrua, R.D. and Igarzabal, C.I.A. Macroporous monolithic supports for affinity chromatography. Journ. Sep. Sci. 34(16-17): 1974-1987 (2011).

Arvidson, P., et al. Chromatography of microbial cells using continuous supermacroporous affinity and ion-exchange columns. Journ. Chromatogr. A 977(1): 27-38 (2002).

Bandari, R., et al. Formation of Pd-nanoparticles within the pores of ring opening metathesis polymerization-derived polymeric monoliths for use in organometallic catalysis. ARKIVOC Online Journ. Org. Chem: 54-70 (2011).

Bandari, R. and Buchmeiser, M.R. Ring-opening metathesis polymerization-derived large-volume monolithic supports for reversed-phase and anion-exchanged chromatography of biomolecules. Analyst 137(14): 3271-3277 (2012).

Bhattacharyya, A. and Klapperich, C.M. Differential gene expression using mRNA isolated on plastic microfluidic chips. Conf. Proc. 31$^{st}$ IEEE EMBS: 1067-1070 (2009).

Binder, J.B., et al. Olefin metathesis in homogeneous aqueous media catalyzed by conventional ruthenium catalysts. Org. Lett. 9(23): 4885-4888 (2007).

Bruchet, A., et al. Synthesis and characterization of ammonium functionalized porous poly(glycidyl methacrylate-co-ethylene dimethacrylate) monoliths for microscale analysis and its application to DNA purification. Journ. Biomed. Nanotechnol. 7(3): 415-425 (2011).

Buchmeiser, M.R. Ring-opening metathesis polymerization-derived materials for separation science, heterogeneous catalysis and tissue engineering. Macromol. Symp. 298(1): 17-24 (2010).

Calabrese, L., et al. Corrosion protection of aluminum 6061 in NaCl solutions by silane-zeolite composite coatings. Journ. Coat. Technol. Res. 9(5): 597-607 (2012).

Caster, K.C., et al. Contact metathesis polymerization (CMP). Journ. Mol. Catal. A Chem. 190(1-2): 65-77 (2002).

Celebi, B., et al. Synthesis of a monolithic, micro-immobilised enzyme reactor via click-chemistry. Anal. Bioanal. Chem. 403(9): 2655-2663 (2012).

Chan, V., et al. The biophysics of DNA hybridization with immobilized oligonucleotide probes. Biophys. Journ. 69(6): 2243-2255 (1995).

Crameri, A. et al. DNA shuffling of a family of genes from diverse species accelerates directed evolution. Nature 391(6664): 288-291 (1998).

Cui, H. and Kessler, M.R. Glass fiber reinforced ROMP-based bio-renewable polymers: enhancement of the interface with silane coupling agents. Comp. Sci. Tech. 72: 1264-1272 (2012).

Dainiak, M.B., et al. Affinity cryogel monoliths for screening for optimal separation conditions and chromatographic separation of cells. Journ. Chromatogr. A 1123(2): 145-150 (2006).

Demel, S., et al. Benchmarking of ruthenium initiators for the ROMP of a norbornenedicarboxylic acid ester. Journ. Mol. Catal. A Chem. 200(1-2): 11-19 (2003).

Dolman, S.J., et al. Supported chiral Mo-based complexes as efficient catalysts for enantioselective olefin metathesis. Journ. Amer. Chem. Soc. 126(35): 10945-10953 (2004).

Evans, R.A. The rise of azide-alkyne 1,3-dipolar 'click' cycloaddition and its application to polymer science and surface modification. Australian Journ. Chem. 60(6): 384-395 (2007).

Fan, L., et al. Rapid preparation and characterization of methacrylate-based monoliths for chromatographic and electrophoretic separation. Journ. Chromatogr. Sci. 48(5): 399-405 (2010).

Gusev, I., et al. Capillary columns with in situ formed porous monolithic packing for micro high-performance liquid chromatography and capillary electrochromatography. Journ. Chromatogr. A 855(1): 273-290 (1999).

Gustavsson, P. and Larsson, P. Continuous superporous agarose beds for chromatography and electrophoresis. Journ. Chromatogr. A 832(1-2): 29-39 (1999).

Gustavsson, P. and Larsson, P. Continuous superporous agarose beds in radial flow columns. Journ. Chromatogr. A 925(1-2): 69-78 (2001).

Hayes, J.D. and Malik, A. Sol-gel monolithic columns with reversed electroosmotic flow for capillary electrochromatography. Anal. Chem. 72(17): 4090-4099 (2000).

Hird, N., et al. Polymer discs—an alternative support format for solid phase synthesis. Tetrahedron 55(31): 9575-9584 (1999).

Hoth, D.C., et al. Metal oxide monolithic columns. Journ. Chromatogr. A 1079(1-2): 392-396 (2005).

Ishizuka, N., et al. Monolithic silica columns for high-efficiency separations by high-performance liquid chromatography. Journ. Chromatogr. A 960(1-2): 85-96 (2002).

Kallury, K.M.R., et al. Silanization of oxidized silicon and aluminum surfaces with functionalized silanes with characterization by wettability, ellipsometry, XPS and quartz crystal microbalance studies. Coll. Surf. 63(1-4): 1-9 (1992).

Kashkary, L., et al. Improved DNA extraction efficiency from low level cell numbers using a silica monolith based micro fluidic device. Anal. Chim. Acta 750: 127-131 (2012).

Kato, M., et al. Effect of preparatory conditions on the performance of photopolymerized sol-gel monoliths for capillary electrochromatography. Journ. Chromatogr. A 961(1): 45-51 (2002).

Konishi, J., et al. Sol-gel synthesis of macro-mesoporous titania monoliths and their applications to chromatographic separation media for organophosphate compounds. Journ. Chromatogr. A 1216(44): 7375-7383 (2009).

Kubo, T., et al. Co-continuous monolithic titania prepared by organic polymer monolith as pore template. Mater. Let. 64(2): 177-180 (2010).

Li, Y. Development of biocompatible polymer monoliths for the analysis of proteins and peptides. Brigham Young University, All Theses and Dissertations, Paper 2073 (2009). Retrieved from the Internet: <URL: http://scholarsarchive.byu.edu/cgi/viewcontent.cgi?article=3072&context=etd>.

Liaw, D., et al. Novel fluorescent polynorbornenes with multi-functional armed structure by using highly stable block macroinitiators via a combination of living ring-opening metathesis polymerization and atom transfer radical polymerization. Polymer 47(9): 3057-3064 (2006).

Lubbad, S., et al. Micropreparative fractionation of DNA fragments on metathesis-based monoliths: influence of stoichiometry on separation. Journ. Chromatogr. A 959(1-2): 121-129 (2002).

Lubbad, S. and Buchmeiser, M.R. Monolithic high-performance SEC supports prepared by ROMP for high-throughput screening of polymers. Macromol. Rapid Comm. 23(10-11): 617-621 (2002).

Lubbad, S.H. and Buchmeiser, M.R. Ring-opening metathesis polymerization-derived monolithic anion exchangers for the fast separation of double-stranded DNA fragments. Journ. Chromatogr. A 1218(17): 2362-2367 (2011).

Lubbad, S.H., et al. Ring-opening metathesis polymerization-derived monolithic strong anion exchangers for the separation of 5'-phosphorylated oligodeoxythymidylic acids fragments. Journ. Chromatogr. A 1218(49): 8897-8902 (2011).

(56) References Cited

OTHER PUBLICATIONS

Luo, Q., et al. Chromatographic separation of proteins on metal immobilized iminodiacetic acid-bound molded monolithic rods of macroporous poly(glycidyl methacrylate-co-ethylene dimethacrylate). Journ. Chromatogr. A 926(2): 255-264 (2011).
Malik, R. and Hage, D.S. Affinity monolith chromatography. Journ. Sep. Sci. 29(12): 1686-1704 (2006).
Martin, J.A., et al. Selection of an aptamer antidote to the anticoagulant drug bivalirudin. PLoS One 8(3): e57341 (2013).
Mayr, B., et al. Metathesis-based monoliths: influence of polymerization conditions on the separation of biomolecules. Anal. Chem. 73(17): 4071-4078 (2001).
Meyer, U., et al. Use of stable free radicals for the sequential preparation and surface grafting of functionalized macroporous monoliths. Macromolecules 33(21): 7769-7775 (2000).
Monzo, A., et al. Optimization of poly(GMA-co-EDMA) monolithic support for trypsin nanoreactor fabrication. Journ. Chromatogr. Sci. 47(6): 467-472 (2009).
Nanci, A., et al. Chemical modification of titanium surfaces for covalent attachment of biological molecules. Journ. Biomed. Res. 40(2): 324-335 (1998).
Nesterenko, E.P., et al. Micro-bore titanium housed polymer monoliths for reversed-phase liquid chromatography of small molecules. Journ. Chromatogr. A 1217(14): 2138-2146 (2010).
Nischang, I., et al. Advances in the preparation of porous polymer monoliths in capillaries and microfluidic chips with focus on morphological aspects. Anal. Bioanal. Chem. 397(3): 953-960 (2010).
Pack, P. and Pluckthun, A. Miniantibodies: use of amphipathic helices to produce functional, flexibly linked dimeric FV fragments with high avidity in *Escherichia coli*. Biochemistry 31(6): 1579-1584 (1992).
Pack, P., et al. Improved bivalent miniantibodies, with identical avidity as whole antibodies, produced by high cell density fermentation of *Escherichia coli*. Bio/technology 11(11): 1271-1277 (1993).
Pack, P., et al. Tetravalent miniantibodies with high avidity assembling in *Escherichia coli*. Journ. Mol. Biol. 246(1): 28-34 (1995).
Pantoja, M., et al. Analysis of hydrolysis process of γ-methacryloxypropyltrimethoxysilane and its influence on the formation of silane coatings on 6063 aluminum alloy. Appl. Surf. Sci. 255(12): 6386-6390 (2009).
Pfaunmiller, E.L., et al. Affinity monolith chromatography: a review of principles and recent analytical applications. Anal. Bioanal. Chem. 405(7): 2133-2145 (2013).
Pflegerl, K., et al. Direct synthesis of peptides on convective interaction media monolithic columns for affinity chromatography. Journ. Comb. Chem. 4(1): 33-37 (2002).
Plieva, F.M., et al. Characterization of polyacrylamide based monolithic columns. Journ. Sep. Sci. 27(10-11): 828-836 (2004).
Plieva, F., et al. Macroporous polyacrylamide monolithic gels with immobilized metal affinity ligands: the effect of porous structure and ligand coupling chemistry on protein binding. Journ. Mol. Recognit. 19(4): 305-312 (2006).
Pohl, C. and Saini, C. Comparison of different synthesis strategies for the preparation of polymeric monoliths for ion chromatography. Pittcon (2007).
Preishuber-Pflugl, P., et al. Surface modification of propene/1,7-octadiene copolymer by metathesis reactions. Journ. Mol. Catal. A Chem. 160(1): 53-61 (2000).
Randon, D.C., et al. Synthesis of zirconia monoliths for chromatographic separations. Journ. Chromatogr. A 1109(1): 19-25 (2006).
Rivera, J.G., et al. Enrichment/isolation of phosphorylated peptides on hafnium oxide prior to mass spectrometric analysis. Analyst 134(1): 31-33 (2009).
Rohr, T., et al. Photografting and the control of surface chemistry in three-dimensional porous polymer monoliths. Macromolecules 36(5): 1677-1684 (2003).
Sabarudin, A., et al. Preparation of methacrylate-based anion-exchange monolithic microbore column for chromatographic separation of DNA fragments and oligonucleotides. Analytica Chimica Acta 736: 108-114 (2012).

Saiki, R.K., et al. Primer-directed enzymatic amplification of DNA with a thermostable DNA polymerase. Science 239(4839): 487-491 (1998).
Satterfield, B.C., et al. Tentacle probe sandwich assay in porous polymer monolith improves specificity, sensitivity and kinetics. Nucl. Acids Res. 36(19): e129 (2008).
Shu, R., et al. Preparation and characterization of lauryl methacrylate-based monolithic microbore column for reversed-phase liquid chromatography. Journ. Chromatogr. A 1218(31): 5228-5234 (2011).
Shu, S., et al. Chemical anchoring of lauryl methacrylate-based reversed phase monolith to 1/16" o.d. polyetheretherktone tubing. Journ. Chromatogr. A 1242: 59-66 (2012).
Simon, R.J., et al. Peptoids: a modular approach to drug discovery. Proc. Nat. Acad. Sci. USA 89(20): 93467-9371 (1992).
Sinitsyna, E.S., et al. Macroporous methacrylate-based monoliths as platforms for DNA microarrays. Talanta 93: 139-146 (2012).
Stachowiak, T.B., et al. Fabrication of porous polymer monoliths covalently attached to the walls of channels in plastic microdevices. Electrophoresis 24(21): 3689-3693 (2003).
Stemmer, W.P. Rapid evolution of a protein in vitro by DNA shuffling. Nature 370(6488): 389-391 (1994).
Stemmer, W.P., et al. Single-step assembly of a gene and entire plasmid from large Numbers of oligodeoxyribonucleotides. Gene 164(1): 49-53 (1995).
Sudheedran, M. and Buchmeiser, M.R. A continuous bioreactor prepared via the immobilization of trypsin on aldehyde-functionalized, ring-opening metathesis polymerization-derived monoliths. Macromolecules 43(23): 9601-9607 (2010).
Sun, X., et al. In-column "click" preparation of hydrophobic organic monolithic stationary phases for protein separation. Anal. Bioanal. Chem. 399(10): 3407-3413 (2011).
Svec, F. Monoliths: a new breed of separation media for chromatography. Lawrence Berkeley National Laboratory.
Svec, F., et al. Rigid macroporous organic polymer monoliths prepared by free radical polymerization. Chapter 2 of Monolithic materials: preparation, properties and applications. Journal of Chromatography Library, vol. 67. Elsevier Science B.V., Amsterdam (2003).
Svec, F. My favorite materials: porous polymer monoliths. Journ. Sep. Sci. 32(1): 3-9 (2009).
Triantafillidis, C., et al. Chemical phase separation strategies towards silica monoliths with hierarchical porosity. Chem. Soc. Rev. 42(9): 3833-3846 (2013).
Tripp, J.A., et al. "Reactive filtration": use of functionalized porous polymer monoliths as scavengers in solution-phase synthesis. Org. Lett. 2(2): 195-198 (2000).
Ueki, Y., et al. Preparation and application of methacrylate-based cation-exchange monolithic columns for capillary ion chromatography. Anal. Chem. 76(23): 7007-7012 (2004).
Ueki, Y., et al. Preparation of low flow-resistant methacrylate-based monolithic stationary phases of different hydrophobicity and the application to rapid reversed-phase liquid chromatographic separation of alkylbenzenes at high flow rate and elevated temperature. Journ. Chromatogr. A 1106(1-2): 106-111 (2006).
Umemura, T., et al. Preparation and characterization of methacrylate-based semi-micro monoliths for high-throughput bioanalysis. Anal. Bioanal. Chem. 386(3): 566-571 (2006).
Uyama, H. Functional polymer monoliths with nanoscale porous structure fabrication and applications. $3^{rd}$ Int. Conf. Nanotek & Expo. (2013).
Vaino, A.R. and Janda, K.D. Euclidean shape-encoded combinatorial chemical libraries. Proc. Nat. Acad. Sci. 97(14): 7692-7696 (2000).
Viklund, C., et al. Monolithic, "molded", porous materials with high flow characteristics for separations, catalysis, or solid-phase chemistry: control of porous properties during polymerization. Chem. Mater. 8(3): 744-750 (1996).
Vlakh, E., et al. Solid phase peptide synthesis on epoxy-bearing methacrylate monoliths. Journ. Pept. Sci. 10(12): 719-730 (2004).
Vlakh, E., et al. Use of monolithic sorbents modified by directly synthesized peptides for affinity separation of recombinant tissue plasminogen activator (t-PA). Journ. Biotech. 107(3): 275-284 (2004).

(56) References Cited

OTHER PUBLICATIONS

Vogelstein, B. and Gillespie, D. Preparative and analytical purification of DNA from agarose. Proc. Nat. Acad. Sci. 76(2): 615-619 (1979).
Wang, M., et al. Preparation and characterization of polyethyleneimine modified ion-exchanger based on poly(methacrylate-co-ethylene dimethacrylate) monolith. Journ. Chromatogr. A 1147(1): 24-29 (2007).
Weisenger, R.M., et al. Mesofulidic devices for DNA-programmed combinatorial chemistry. PLoS One 7(3): 1-8 (2012).
Wieder, W., et al. Novel monolithic poly(p-methylstyrene-co-bis(p-vinylbenzyl)dimethylsilane) capillary columns for biopolymer separation. Journ. Chromatogr. A 1191(1-2): 253-262 (2008).
Wrenn, S.J. and Harbury, P.B. Chemical evolution as a tool for molecular discovery. Annu. Rev. Biochem. 76: 331-349 (2007).
Wrenn, S.J., et al. Synthetic ligands derived by in vitro selection. Journ. Amer. Chem. Soc. 129(43): 13137-13143 (2007).
Wu, R., et al. Recent development of monolithic stationary phases with emphasis on microscale chromatographic separation. Journ. Chromatogr. A 1184(1-2): 369-392 (2008).
Wu, M., et al. "One-pot" fabrication of clickable monoliths for enzyme reactors. Chem. Commun. 49(14): 1407-1409 (2013).
Wysoczynski, C.L., et al. Reversed-phase ion-pair liquid chromatography method for purification of duplex DNA with single base pair resolution. Nucl. Acids Res. 41(20): e194 (2013).
Xie, S., et al. Preparation of porous hydrophilic monoliths: effect of the polymerization conditions on the porous properties of poly (acrylamide-co-N,N'-methylenebisacrylamide) monolithic rods. Journal of Polymer Science Part A: Polymer Chemistry 35(6): 1013-1021 (1997).
Xie, S., et al. Design of reactive porous polymer supports for high throughput bioreactors: poly(2-vinyl-4,4-dimethylazlactone-co-acrylamide-co-ethylene dimethacrylate) monoliths. Biotechnol. Bioeng. 62(1): 30-35 (1999).
Xie, S., et al. Porous polymer monoliths: an alternative to classical beads. Chapter: Modern Advances in Chromatography. Advances in Biochemical Engineering/Biotechnology, vol. 76: 87-125. Springer-Verlag, Berlin (2002).
Yu, C., et al. Monolithic porous polymer for on-chip solid-phase extraction and preconcentration prepared by photoinitiated in situ polymerization within a microfluidic device. Anal. Chem. 73(21): 5088-5096 (2001).
Zhu, D. and Van Ooij, W.J. Overview: corrosion control of metals by a novel environmentally-friendly silane treatment. Capatue Chemical.
Integrated DNA Technologies. Strategies for attaching oligonucleotide to solid supports (2011).
HoloDiag Solid State Solutions. www.holodiag.com.
Acquah, C., et al. A review on immobilised aptamers for high throughput biomolecular detection and screening. Analytica Chimica Acta (2015), doi: 10.1016/j.aca.2015.05.050.
Brothier, F., et al. Miniaturized DNA aptamer-based monolithic sorbent for selective extraction of a target analyte coupled on-line to nanoLC. Anal Bioanal Chem 406:7875-7886 (2014).
Chen, Y., at al. Aptamer functionalized hydrophilic polymer monolith with gold nanoparticles modification for the sensitive detection of human α-thrombin. Talanta http://dx.doi.org/10.1016/j.talanta. 2016.02.054 (2016).
Chopra, A., et al. Aptamers as an emerging player in biology. Aptamers and Synthetic Antibodies. 1(1): 1-11 (2014).
Deng, N., et al. Aptamer Modified Organic—Inorganic Hybrid Silica Monolithic Capillary Columns for Highly Selective Recognition of Thrombin. Anal. Chem. 84: 10186-10190 (2012).
Gao, C., et al. Fluorescent measurement of affinity binding between thrombin and its aptarners using on-chip affinity monoliths. J. of Chromatography A. 1291: 92-96 (2013).
Geiser, L., et al. In-line system containing porous polymer monoliths for protein digestion with immobilized pepsin, peptide preconcentration and nano-liquid chromatography separation coupled to electrospray ionization mass spectroscopy. J. of Chromatography A. 1188: 88-96 (2008).
Han, B., et al. High performance aptamer affinity chromatography for single-step selective extraction and screening of basic protein lysozyme. J. of Chromatography B. 903: 112-117 (2012).
Marechal, A., et al. In-line coupling of an aptarner based miniaturized monolithic affinity preconcentration unit with capillary electrophoresis and Laser Induced Fluorescence detection. J. of Chromatography A, 1406:109-117 (2015).
Petro, M., et al. Monodisperse hydrolyzed poly(glycidyl methacrylate-co-ethylene dimethacrylate) beads as a stationary phase for normal-phase HPLC. Anal. Chem. 69: 3131-3139 (1997).
Pichon, V., et al. Aptamer-based-sorbents for sample treatment—a review, Anal Bioanal Chem (2014) DOI 10.1007/s00216-014-8129-5.
Rohr, T., et al. Surface functionalization of thermoplastic polymers for the fabrication of microfluidic devices by photoinitiated grafting. Adv. Funct. Mater. 13(4): 264-270 (2003).
Satterfield, B., et al. Microfluidic Purification and Preconcentration of mRNA by Flow-Through Polymeric Monolith. Anal. Chem. 79: 6230-6235 (2007).
Slater. M., et al. "Click chemistry" in the preparation of porous polymer-based particulate stationary phases for µ-HPLC separation of peptides andpProteins. Anal. Chem. 78: 4969-4975 (2006).
Svec, F. Quest for organic polymer-based monolithic columns affording enhanced efficiency in high performance liquid chromatography separations of small molecules in isocratic mode. J Chromatogr A. 1228: 250-262 (2012).
Vonk, R., et al. Titanium-scaffolded organic-monolithic stationary phases forultra-high-pressure liquid chromatography. Journal of Chromatography A 1359: 162-169 (2014).
Wang, Z., et al. Aptarner-based organic-silica hybrid affinity monolith prepared via "thiol-ene" click reaction for extraction of thrombin. Talanta http://dx.doi.org/10.1016/j.talanta.2015.02.009 (2015).
Xu, L., et al. Porous monoliths: sorbents for miniaturized extraction in biological analysis. Anal Bioanal Chem. 399:3345-3357 (2011).
Zhao, Q., et al. Aptamer-modified monolithic capillary chromatography for protein separation and detection. Anal. Chem. 80: 3915-3920 (2008).
Zhao, Q., et al. Aptamer-based affinity chromatographic assays for thrombin. Anal. Chem. 80: 7586-7593 (2008).
Clark, M.A., et al. Design, synthesis and selection of DNA-encoded small-molecule libraries. Nature Chemical Biology. 5(9): 647-654 (2009).
Deng, H., et al. Discovery of Highly Potent and Selective Small Molecule ADAMTS-5 Inhibitors That Inhibit Human Cartilage Degradation via Encoded Library Technology (ELT). J. Med. Chem. 55: 7061-7079 (2012).
Halpin, D.R. and Harbury, P.B. DNA Display I. Sequence-Encoded Routing of DNA Populations. PLoS Biology. 2(7): 1015-1021 (2004).
Halpin, D.R. and Harbury, P.B. DNA Display II. Genetic Manipulation of Combinatorial Chemistry Libraries for Small-Molecule Evolution. PLoS Biology. 2(7): 1022-1030 (2004).
Halpin, D.R., et al., DNA Display III. Solid-Phase Organic Synthesis on Unprotected DNA. PLoS Biology. 2(7): 1031-1038 (2004).
Weisinger, R.M., et al. Highly Parallel Translation of DNA Sequences into Small Molecules. PLoS One 7(3): e28056 (2012).
Extended European Search Report for European Patent Application No. EP 15743623.9, dated Aug. 21, 2017, 8 Pages.
Jas, G., et al., "Continuous Flow Techniques in Organic Synthesis," Chemistry A European Journal, Dec. 5, 2003, pp. 5708-5723, vol. 9, No. 23.
PCT Search Report and Witten Opinion for PCT/US15/13382, dated Apr. 23, 2015, 10 Pages.
Search Report for Singapore Patent Applications No. 11201606921P, dated Sep. 13, 2017, 9 Pages.
Sekar, M., et al., "Comparative study of sequence-dependent hybridization kinetics in solution and on microspheres," Nucleic Acids Research, 2005. vol. 33, No. 1, pp. 366-375.

\* cited by examiner

MONOLITHS WITH ATTACHED RECOGNITION COMPOUNDS, ARRAYS THEREOF AND USES THEREOF

This application claims priority under 35 U.S.C. § 119(e) from U.S. Provisional Application Ser. Nos. 61/932,747 and 62/006,845, filed Jan. 28, 2014 and Jun. 2, 2014, respectively, which are hereby incorporated by reference in their entirety.

FIELD

Provided herein are monoliths with attached recognition compounds which selectively bind ligands, methods of preparing such monoliths, arrays thereof and uses thereof. For example, monoliths provided herein can be used in columns and arrays thereof.

BACKGROUND

Crosslinked polymer supports have been useful in catalysis, separations and solid phase synthesis. Crosslinked polymer supports were initially provided as homogeneous porous particles, which were typically used in continuous flow processes including, inter alia, chromatography. However, a number of significant issues exist with respect to the use of particulate sorbents: slow exchange between convective flow and binding to the solid support which leads to poor resolution, large void volume between packed particles, high back pressures and low dynamic binding capacity, particularly for macromolecules. The above limitations have restricted the use of homogeneous porous particles as functionalized supports with attached recognition molecules which can bind various ligands.

More recently, porous monolithic materials have been developed (Arrua, et al., *Materials* (2009) 2 2429-2466; Svec et al., *Monolith Materials*, J. of Chromatography Library, Vol. 67, Svec et al., (Eds.); Wu et al., *J. Chromatography A* (2008) 369-392). These heterogeneous macroporous polymers have a rigid porous structure which is formed during preparation and is usually maintained in any solvent or in a dry state and imparts a sponge like quality to the monolith. Importantly, the problems of large void volumes (i.e., high permeability), slow exchange (i.e., poor rates of mass transfer) of macromolecules, poor resolution and high back pressures are mitigated in such monolithic materials where fluid flow is through the pores of the monolith. Currently, monoliths have been used mainly for chromatographic separations with relatively little attention devoted to the preparation of monoliths functionalized with attached recognition molecules (particularly, DNA) for ligand binding and use, for example, in arrays.

Accordingly, what is needed are monoliths which include attached recognition compounds and arrays of these monoliths Such monoliths and arrays thereof will be useful, inter alia, in ligand binding.

SUMMARY

The present invention provides monoliths functionalized with recognition compounds, arrays thereof and uses thereof. In one aspect, monoliths which have attached recognition compounds are provided. The recognition compounds selectively bind ligands. In some embodiments, the recognition compounds are oligonucleotides, single stranded RNA, single stranded DNA, DNA binding proteins, RNA binding proteins, peptide nucleic acids, peptides, depsipeptides, polypeptides, antibodies, peptoids, polymers, polysiloxanes, inorganic compounds of molecular weight greater that 50 daltons, organic compounds of molecular weight between about 3000 daltons and about 50 daltons or combinations thereof. In other embodiments, the ligands are oligonucleotides, single stranded RNA, single stranded DNA, DNA binding proteins, RNA binding proteins, peptide nucleic acids, peptides, depsipeptides, polypeptides, antibodies, peptoids, polymers, polysiloxanes, inorganic compounds of molecular weight greater that 50 daltons, organic compounds of molecular weight between about 3000 daltons and about 50 daltons or combinations thereof.

In some embodiments, a housing is provided which includes a monolith which encompasses attached recognition compounds that selectively bind ligands. In other embodiments, the housing selectively binds members of compound libraries, which may be provided by phage display, RNA display or nucleic acid programmable combinatorial chemistry.

In some embodiments, an array is provided. The array encompasses two or more housings which include a monolith which includes attached recognition compounds that selectively bind ligands. In other embodiments, the array includes a block which encompasses two or more wells which contain housings. The housings include a monolith which encompasses attached recognition compounds that selectively bind ligands.

In still another aspect, a monolith media is provided. The monolithic media includes aggregated particles with attached recognition compounds which selectively bind ligands.

In still another aspect, an array including two or more ion exchange housings is provided. The ion exchange housings include a monolith with an ionizable group. In some embodiments, the array includes filter plates or any other type of microplates or devices which allow for flow through of the mobile phase and a block which encompasses two or more wells which contain ion exchange material. The ion exchange material encompasses a monolith which includes an ionizable group.

In yet another aspect, a method for preparing a nucleic acid programmed library of chemical compounds is provided. The method encompasses the steps of contacting a mixture of nucleic acid molecules with an array including a block which has two or more addressable wells. Each well includes a monolith with one or more attached recognition compounds which selectively bind single stranded nucleic acids thereby splitting the nucleic acid molecules into subpopulations. The subpopulations of nucleic acid molecules may optionally be dissociated from the recognition compounds, using, for example, elevated temperature, change in ionic strength or change in pH with the dissociated nucleic acid molecules transferred to separate containers. The separated subpopulations of nucleic acid molecules are then reacted with different chemical subunits, where the nucleic acid molecules include at least one binding sequence and one chemical reaction site. When the subpopulations of nucleic acid molecules are optionally transferred to separate containers the wells which include monoliths with attached recognition compounds which selectively bind nucleic acids are aligned in addressable manner with the separate containers.

In still another aspect, a method for preparing a nucleic acid programmed library of chemical compounds is provided. The method encompasses the steps of contacting a mixture of nucleic acid molecules with an array including a block which has two or more addressable wells. Each well includes a monolith with one or more attached recognition compounds which selectively bind single stranded nucleic acids thereby splitting the nucleic acid molecules into subpopulations. The subpopulations of nucleic acid molecules are transferred to a second array including filter plates or any other type of microplates or devices which allow for flow through of the mobile phase and a block containing two or more addressable wells. The subpopulations of nucleic acid molecules may be dissociated from the recognition compounds using, for example, elevated temperature, change in ionic strength or change in pH. The wells of the second array include anion exchange material which non-specifically immobilizes the subpopulations of nucleic acid molecules. The immobilized subpopulations of nucleic acid molecules are reacted with different chemical subunits. The wells which include monoliths with one or more attached recognition compounds which selectively bind nucleic acids are aligned in addressable manner with the wells including the anion exchange material. The nucleic acid molecules include at least one binding sequence and one chemical reaction site. In some embodiments, the anion exchange material includes a monolith with anion exchange groups.

In still another aspect, a device is provided. The device encompasses two arrays which include separate blocks. The block of the first array encompasses two or more addressable wells which include monoliths with attached recognition compounds which selectively bind ligands. The block of the second array includes filter plates or any other type of microplates or devices which allow for flow through of the mobile phase and two or more addressable wells which include ion exchange material. The wells which include monoliths with attached recognition compounds which selectively bind ligands are aligned with the wells including the ion exchange material. In some embodiments, the ion exchange material includes a monolith with ion exchange groups.

DETAILED DESCRIPTION

Definitions

Figure 1:
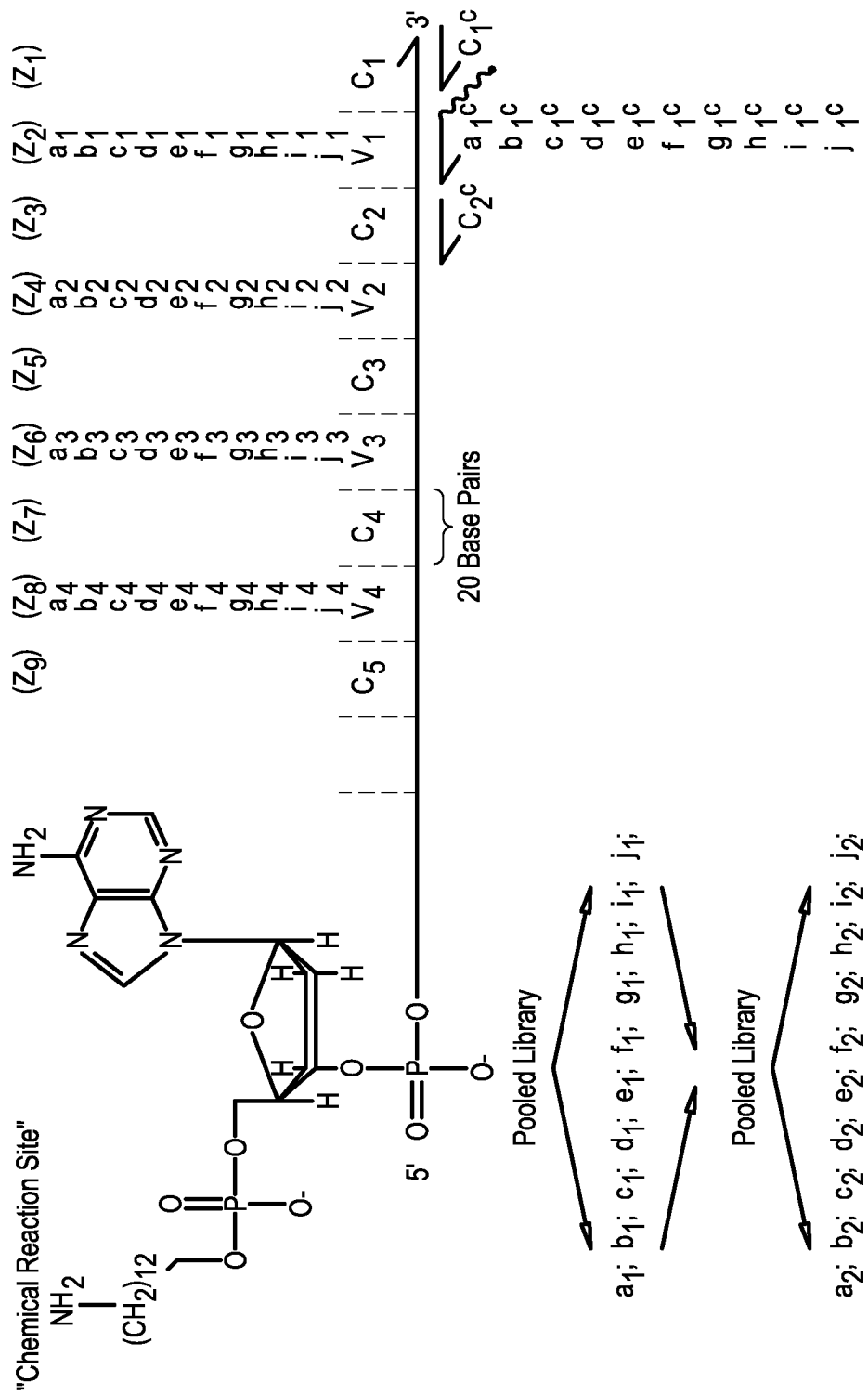
FIG. 1 shows an exemplary DNA-directed splitting of a library of fragments. The degenerate family of nucleic acid tags in this example is composed of catenated 20 base-pair nucleotide sequences, which are either constant ($C_1$-$C_5$) or variable ($a_1$-$j_4$). The letters $a_1$ through $j_4$ in the variable regions of the DNA fragments denote distinct 20 nucleotide sequences with orthogonal hybridization properties. To carry out the first split, the degenerate family of fragments is passed over a set of ten different affinity resins displaying the sequences $a_1^c$-$j_1^c$, which are complementary to the sequences $a_1$-$j_1$ in the first variable region (an exemplary affinity resin is represented by the circle). Ten sub-pools of the original family of fragments result. Each sub-pool of nucleic acid tags is then reacted with a distinct chemical monomer to allow for coupling of the distinct chemical monomer at the chemical reaction site of each nucleic acid tag. The sub-pools are then recombined, and the library is split into a new set of sub-pools based on the sequences $a_2$-$j_2$, etc.

Unless defined otherwise, all technical and scientific terms used herein have the same meaning as is commonly understood by one of ordinary skill in the art to which this invention belongs. In the event that a plurality of definitions for a term exists, those in this section prevail unless stated otherwise.

It must be noted that as used herein and in the appended claims, the singular forms "a", "an" and "the" include plural referents unless the context, clearly dictates otherwise. Thus, for example, reference to "a tag" includes a plurality of such tags and reference to "the compound" includes reference to one or more compounds and equivalents thereof known to those skilled in the art, and so forth.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

"Alkyl" as used herein means any saturated or unsaturated, branched or unbranched, cyclized, or combination thereof, typically having 1-10 carbon atoms, which includes methyl, ethyl, propyl, isopropyl, butyl, isobutyl, t-butyl, pentyl, cyclopentyl, isopentyl, neopentyl, hexyl, isohexyl, cyclohexyl, which may be optionally substituted with methyl.

"Alkylene" as used herein means any branched or unbranched, cyclised, or combination thereof, typically having 1-10 carbon atoms, which includes methyl, ethyl, propyl, isopropyl, butyl, isobutyl, t-butyl, pentyl, cyclopentyl, isopentyl, neopentyl, hexyl, isohexyl, cyclohexyl, which may be optionally substituted with methyl.

"Amplifying population of compounds" as used herein refers to an increasing population of compounds synthesized according to the catenated hybridization sequences of the nucleic acid tags produced by the iterative methods described herein.

"Antibody" as used herein refers to a protein comprising one or more polypeptides substantially or partially encoded by immunoglobulin genes or fragments of immunoglobulin genes, e.g., a fragment containing one or more complementarity determining region (CDR). The recognized immunoglobulin genes include the kappa, lambda, alpha, gamma, delta, epsilon and mu constant region genes, as well as myriad immunoglobulin variable region genes. Light chains are typically classified as either, e.g., kappa or lambda. Heavy chains are typically classified e.g., as gamma, mu, alpha, delta, or epsilon, which in turn define the immunoglobulin classes, IgG, IgM, IgA, IgD and IgE, respectively. A typical immunoglobulin (antibody) structural unit comprises a tetramer. In nature, each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases. Thus, for example, pepsin digests an antibody below the disulfide linkages in the hinge region to produce F(ab)'2 (fragment antigen binding) and Fc (fragment crystallizable, or fragment complement binding). F(ab)'2 is a dimer of Fab, which itself is a light chain joined to VH-CH1 by a disulfide bond. The F(ab)'2 may be reduced under mild conditions to break the disulfide linkage in the hinge region thereby converting the $(Fab')_2$ dimer into a Fab' monomer. The Fab' monomer is essentially a Fab with part of the hinge region. The Fc portion of the antibody molecule corresponds largely to the constant region of the immunoglobulin heavy chain, and is responsible for the antibody's effector function (see, *Fundamental Immunology*, $4^{th}$ edition. W. E. Paul. ed. Raven Press, N.Y. (1998), for a more detailed description of antibody fragments). While various antibody fragments are defined in terms of the digestion of an intact antibody, one of skill will appreciate that such Fab' or Fc fragments may be synthesized de novo either chemically or by utilizing recombinant DNA methodology, peptide display, or the like. Thus, the term antibody, as used herein, also includes antibody fragments either produced by the modification of whole antibodies or synthesized de novo using recombinant DNA methodologies. Antibodies also include single-armed composite monoclonal antibodies, single chain antibodies, including single chain Fv (sFv) antibodies in which a variable heavy and a variable light chain are joined together (directly or through a peptide linker) to form a continuous polypeptide, as well as diabodies, tribodies, and tetrabodies (Pack et al. (1995) *J Mol Biol* 246:28; *Biotechnol* 11:1271; and *Biochemistry* 31:1579). The antibodies are, e.g., polyclonal, monoclonal, chimeric, humanized, single chain, Fab fragments, fragments produced by an Fab expression library, or the like.

"Base-specific duplex formation" or "specific hybridization" as used herein refer to temperature, ionic strength and/or solvent conditions effective to produce sequence-specific pairing between a single-stranded oligonucleotide and its complementary-sequence nucleic acid strand, for a given length oligonucleotide. Such conditions are preferably stringent enough to prevent or largely prevent hybridization of two nearly-complementary strands that have one or more internal base mismatches. In some embodiments, the region of identity between two sequences forming a base-specific duplex is greater than about 5 bp. In other embodiments, the region of identity is greater than 10 bp.

"Capture nucleic acid", "capture oligonucleotide", "and immobilized capture nucleic acid" as used herein refer to a nucleic acid sequence attached to a monolith. In general, the sequence of a capture nucleic acid is complementary to one of the different hybridization sequences (e.g., $a_1$, $b_1$, $c_1$, etc.) of the nucleic acid tags and therefore allows for sequence-specific splitting of a population of nucleic acid tagged molecules into a plurality of sub-populations of distinct nucleic acid tagged molecules in separate containers.

"Chemical reaction site" as used herein refers to a chemical component of a nucleic acid tag capable of forming a variety of chemical bonds including, but not limited to; amide, ester, urea, urethane, carbon-carbonyl bonds, carbon-nitrogen bonds, carbon-carbon single bonds, olefin bonds, thioether bonds, and disulfide bonds.

"Combinatorial library" as used herein refers to a library of molecules containing a large number, typically between $10^3$ and $10^{15}$ or more different compounds typically characterized by different sequences of subunits, or a combination of different side chains functional groups and linkages.

"DAEM" as used herein refers to 2(dimethylamino)ethyl methacrylate.

"DEGDMA" as used herein refers to diethylene glycol dimethacrylate.

"Depsipeptide" as used herein refers to a peptide as defined herein where one or more of amide bonds are replaced by ester bonds.

"Different-sequence small-molecule compounds" refers to small organic molecules, typically, but not necessarily, having a common parent structure, such as a ring structure, and a plurality of different R group substituents or ring-structure modifications, each of which takes a variety of forms, e.g., different R groups. Such compounds are usually non-oligomeric (i.e., do not consist of sequences of repeating similar subunits) and may be similar in terms of basic structure and functional groups, but vary in such aspects as chain length, ring size or number, or patterns of substitution.

"EDMA" as used herein refers to ethylene glycol dimethacrylate.

"Genetic recombination of nucleic acids tags" as used herein refers to forming chimeras of nucleic acid tags derived from compounds having one or more desired activities. Chimeras can be formed by genetic recombination, after repeated cycles of enrichment and step-wise synthesis, PCR amplification and step-wise synthesis, partial digestion, reformation and stepwise synthesis to yield a highly enriched subpopulation of nucleic acid tags which are bound to compounds having one or more desired activities.

"GMA" as used herein refers to glycidyl methacrylate.

"HEMA" as used herein refers to 2-hydroxyl ethyl methacrylate.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202-205 in *Polymorphism in Pharmaceutical Solids*, (Brittain, H. ed.), Marcel Dekker, Inc., New York, N.Y., 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-Ray diffraction, X-Ray powder diffraction, Polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routinely offer services that include preparation and/or characterization of hydrates such as, for example, HOLODIAG, Pharmaparc II, Voie de l'Innovation, 27 100 Val de Reuil, France (http://www.holodiag.com).

"Ligand" as used herein refers to a oligonucleotide, single stranded RNA, single stranded DNA, a DNA binding protein, a RNA binding protein, a peptide nucleic acid, a peptide, a depsipeptide, a polypeptide, a antibody, a peptoid, a polymer, a polysiloxane, a inorganic compound of molecular weight greater that 50 daltons, a organic compound of molecular weight between about 1000 daltons and about 50 daltons or a combination thereof.

"Linker" as used herein is any molecule or substance which performs the function of linking the monolith to the recognition compound. A linker may vary in structure and length. The linker may be hydrophobic or hydrophilic, long or short, rigid, semirigid or flexible, etc. The linking group can comprise, for example, a polymethylene chain, such as a —$(CH_2)_n$— chain or a poly(ethylene glycol) chain, such as a —$(CH_2CH_2O)_n$ chain, where in both cases n is an integer from 1 to about 20, 5'-O-Dimethoxytrityl-1',2'-Dideoxyribose-3'-[(2-cyanoethyl)-(N,N-diisopropyl)]-phosphoramidite; 9-O-Dimethoxytrityl-triethylene glycol,1-[(2-cyanoethyl)-(N,N-diisopropyl)]-phosphoramidite; 3-(4,4'-Dimethoxytrityloxy)propyl-1-[(2-cyanoethyl)-(N,N-diisopropyl)]-phosphoramidite; and 18-O-Dimethoxytritylhexaethyleneglycol, 1,-[(2-cyanoethyl)-(N,N-diisopropyl)]-phosphoramidite, amino-carboxylic linkers (e.g., peptides (e.g., Z-Gly-Gly-Gly-Osu or Z-Gly-Gly-Gly-Gly-Gly-Gly-Osu), PEG (e.g., Fmoc-aminoPEG2000-NHS or amino-PEG (12-24)-NHS), or alkane acid chains (e.g., Boc-ε-aminocaproic acid-Osu)), click chemistry linkers (e.g., peptides (e.g., azidohomalanine-Gly-Gly-Gly-OSu or propargylglycine-Gly-Gly-Gly-OSu), PEG (e.g., azido-PEG-NHS), or alkane acid chains (e.g., 5-azidopentanoic acid, (S)-2-(azidomethyl)-1-Boc-pyrrolidine, or 4-azido-butan-1-oic acid N-hydroxysuccinimide ester)), thiol-reactive linkers (e.g., PEG (e.g., SM(PEG)n NHS-PEG-maleimide), alkane chains (e.g., 3-(pyridin-2-yldisulfanyl)-propionic acid-Osu or sulfosuccinimidyl 6-(3'-[2-pyridyldithio]propionamido)hexanoate))), amidites for oligonucleotide synthesis (e.g., amino modifiers (e.g., 6-(trifluoroacetylamino)-hexyl-(2-cyanoethyl)-(N,N-diisopropyl)-phosphoramidite), thiol modifiers (e.g., S-trityl-6-mercaptohexyl-1-[(2-cyanoethyl)-(N,N-diisopropyl)]-phosphoramidite, or chick chemistry modifiers (e.g., 5-hexynl-TTT(T)$_{0-7}$, 6-hexynl-TTT(T)$_{0-7}$, 5-hexyn-1-yl-(2-cyanoethyl)-(N,N-diisopropyl)-phosphoramidite, 6-hexyn-1-yl-(2-cyanoethyl)-(N,N-diisopropyl)-phosphoramidite, 3-dimethoxytrityloxy-2-(3-(3-propargyloxypropanamido)propanamido)propyl-1-O-succinoyl, long chain alkylamino CPG, or 4-azido-butan-1-oic acid N-hydroxysuccinimide ester)).

"Initiator" as used herein refers to any free radical generator capable of initiating polymerization of monovinyl monomers or polyvinyl monomers by way of thermal, photo, or redox initiation. "MAA" as used herein refers to methacrylic acid.

"MAETA" as used herein refers to [2-(methacryloxy)ethyl]trimethyl ammonium chloride.

"γ-MAPS" as used herein refers to 3-(trimethoxysilyl)propyl methacrylate.

"Monolith" as used herein refers to a continuous stationary phase (i.e., a single continuous material (e.g., a polymer or silica base matrix) that contains large interconnected pores or channels allowing high flow rates of mobile phases at moderate pressure.

"Monolithic media" as used herein refers to a packing of aggregated particles which has significantly lower column pressure than expected on the basis of particle size.

"NBE" as used herein refers to norborn-2-ene.

"Non-specific binding" as used herein with respect to a "non-specific monolith" refer to binding of nucleic acid that does not depend on the nucleic acid sequence applied to the monolith. Exemplary materials for non-specific binding include ion-exchange materials, which are effective to non-specifically capture nucleic acid tagged molecules at one ionic strength and release the nucleic acid tagged molecules, following molecule reaction, at a higher ionic strength.

"Nucleic acid" as used herein refers to a oligonucleotide analog as defined below as well as a double stranded DNA and RNA molecule. A DNA and RNA molecule may include the various analogs defined below.

"Nucleic acid tag-directed synthesis" or "tag-directed synthesis" or "chemical translation" as used herein refer to synthesis of a plurality of compounds based on the catenated hybridization sequences of the nucleic acid tags according to the methods disclosed herein.

"Nucleic acid tag", "nucleic acid support", "synthesis-directing nucleic acid tags", and "DNA-tag" as used herein mean the nucleic acid sequences which each comprise at least (i) a different first hybridization sequence, (ii) a different second hybridization sequence, and (iii) a chemical reaction site. The "hybridization sequences" refer to oligonucleotides comprising between about 3 and up to 50, and typically from about 5 to about 30 nucleic acid subunits. Such "nucleic acid tags" are capable of directing the synthesis of the combinatorial library based on the catenated hybridization sequences.

"Oligonucleotides" or "oligos" as used herein refer to nucleic acid oligomers containing between about 3 and up to about 50, and typically from about 5 to about 30 nucleic acid subunits. In the context of oligos (e.g., hybridization sequence) which direct the synthesis of library compounds, the oligos may include or be composed of naturally-occurring nucleotide residues, nucleotide analog residues, or other subunits capable of forming sequence-specific base pairing, when assembled in a linear polymer, with the proviso that the polymer is capable of providing a suitable substrate for strand-directed polymerization in the presence of a polymerase and one or more nucleotide triphosphates, e.g., conventional deoxyribonucleotides. A "known-sequence oligo" is an oligo whose nucleic acid sequence is known.

"Oligonucleotide analog" as used herein refers to a nucleic acid that has been modified and which is capable of some or all of the chemical or, biological activities of the oligonucleotide from which it was derived. An oligonucleotide analog will generally contain phosphodiester bonds, although in some cases, oligonucleotide analogs are included that may have alternate backbones. Modifications of the ribose-phosphate backbone may facilitate the addition of additional moieties such as labels, or may be done to increase the stability and half-life of such molecules. In addition, mixtures of naturally occurring nucleic acids and analogs can be made. Alternatively, mixtures of different nucleic acid analogs, and mixtures of naturally occurring nucleic acids and analogs may be made. The oligonucleotides may be single stranded or double stranded, as specified, or contain portions of both double stranded or single stranded sequence. The oligonucleotide may be DNA, RNA or a hybrid, where the nucleic acid contains any combination of deoxyribo- and ribo-nucleotides, and any combination of bases, including uracil, uridine, adenine, thymine, cytosine, guanine, inosine, xathanine hypoxathanine, isocytosine, isoguanine, etc.

"Peptide" as used herein refers to a polymer of amino acid residues between about 2 and 50 amino acid residues, between about 2 and 20 amino acid residues, or between about 2 and 10 residues. Peptides include modified peptides such as, for example, glycopeptides, PEGylated peptides, lipopeptides, peptides conjugated with organic or inorganic ligands, peptides which contain peptide bond isosteres (e.g., ψ[([CH$_2$S], ψ(CH$_2$NH$_2$], ψ[NHCO], ψ[COCH$_2$], ψ[(E) or (Z) CH═CH], etc and also include cyclic peptides. In some embodiments, the amino acid residues may be any L-α-amino acid, D-α-amino residue, N-alkyl variants thereof or combinations thereof. In other embodiments, the amino acid residues may any L-α-amino acid, D-α-amino residue, R-amino acids. T-amino acids, N-alkyl variants thereof or combinations thereof.

"Operatively linked" as used herein refers to at least two chemical groups or structures that are linked together. For example, an oligonucleotide may be covalently attached through a linker to a ligand or a chemical reaction site. In some embodiments, the groups or structures may remain linked together through various manipulations, such as, for example, the steps of a process.

"Peptide nucleic acid" as used herein refers to oligonucleotide analogues where the sugar phosphate backbone of nucleic acids has been replaced by pseudopeptide skeleton (e.g., N-(2-aminoethyl)-glycine)(Nielsen et al., U.S. Pat. No. 5,539,082; Nielsen et al., U.S. Pat. No. 5,773,571; Burchardt et al., U.S. Pat. No. 6,395,474).

"Peptoid" as used herein refers to polymers of poly N-substituted glycine (Simon et al., *Proc. Natl. Acad. Sci.* (1992) 89(20) 9367-9371) and include cyclic variants thereof.

"Polypeptide" as used herein refers to a polymer of amino acid residues typically comprising greater than 50 amino acid residues and includes cyclic variants thereof. Polypeptide includes proteins (including modified proteins such as glycoproteins, PEGylated proteins, lipoproteins, polypeptide conjugates with organic or inorganic ligands, etc.) receptor, receptor fragments, enzymes, structural proteins (e.g., collagen) etc. In some embodiments, the amino acid residues may be any L-α-amino acid, D-α-amino residue, or combinations thereof. In other embodiments, the amino acid residues may be any L-α-amino acid, D-α-amino residue, N-alkyl variants thereof or combinations thereof.

"Polymer" includes copolymer, and the term "monomer" includes co-monomer. Polymers include, for example, polyamides, phospholipids, polycarbonates, polysaccharides, polyurethanes, polyesters, polyureas, polyacetates, polyarylene sulfides, polyethylenimines, polyimides, etc.

"Porogen" or "porogenic solvent" as used herein refers to a solvent capable of forming pores in a polymer matrix during polymerization thereof, and includes but is not limited to a aliphatic hydrocarbon, a aromatic hydrocarbon, a ester, a amide, a alcohol, a ketone, a ether, a solutions of soluble polymer, and a combination thereof.

"Recognition Compound" as used herein refers to a oligonucleotide, single stranded RNA, single stranded DNA, a DNA binding protein, a RNA binding protein, a peptide nucleic acid, a peptide, a depsipeptide, a polypeptide, a antibody, a peptoid, a polymer, a polysiloxanes, a inorganic compounds of molecular weight greater that 50 daltons, a organic compounds of molecular weight between about 1000 daltons and about 50 daltons or a combination thereof.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. In some embodiments, salts may be formed when an acidic proton present can react with inorganic bases (e.g., sodium hydroxide, sodium carbonate, potassium hydroxide, aluminum hydroxide, calcium hydroxide, etc.) and organic bases (e.g., ethanolamine, diethanolamine, triethanolamine, tromethamine, N-methylglucamine, etc.) In some embodiments, the salt is pharmaceutically acceptable.

"Solvates" refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 205-208 in *Polymorphism in Pharmaceutical Solids*, (Brittain, H. ed.), Marcel Dekker, Inc., New York, N.Y., 1999)). The above methods for preparing solvates are well within the ambit of those of skill in the art, are completely conventional do not require any experimentation beyond what is typical in the art. Solvates may be characterized and/or analyzed by methods well known to those of skill in the art such as, for example, single crystal X-Ray diffraction, X-Ray powder diffraction, Polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routinely offer services that include preparation and/or characterization of solvates such as, for example, HOLODIAG, Pharmaparc II, Voie de l'Innovation, 27 100 Val de Reuil, France (http://www.holodiag.com).

"Selection for a desired activity" as used herein is any biochemical procedure that segregates more desirable molecules from less desirable molecules based on physical properties of the molecule. As such it included physical segregation of compounds that exhibit a desired property from a heterogeneous mixture of molecules. Examples include affinity purification of ligands from mixtures by binding to an immobilized target protein, or isolation of enzyme substrates from mixtures by enzyme-mediated attachment of an affinity handle, etc.

"SPMA" as used herein refers to 3-sulfopropyl methacrylate.

"TRIM" as used herein refers to trimethylolpropane trimethacrylate.

"Tagged compounds". "DNA-tagged compound", or "nucleic acid-tagged compound" are used to refer to compounds containing (a) unique nucleic acid tags, each unique nucleic acid tag of each compound includes at least one and preferably two or more catenated different hybridization sequences, wherein the hybridization sequences are capable of binding specifically to complementary immobilized capture nucleic acid sequences, and (b) a chemically reactive reaction moiety that may include a compound precursor, a partially synthesized compound, or completed compound. A nucleic acid tagged compound in which the chemically reactive moiety is a completed-synthesis compound is also referred to as a nucleic acid-tagged compound Monoliths with Attached Recognition Compounds and Arrays Thereof Monoliths are integrated continuous porous media without interparticular voids which have been typically used as chromatographic supports (e.g., Ueki et al., *Anal. Chem.* (2004) 76, 7007-7012; Ueki et al., *J. Chromatography A* (2006) 1106, 106-111; Saburadin et al., *Analytica Chimica Acta* (2012) 736 108-114; Shu et al., *J. Chromatography A* (2011) 1218 5288-5234; Lubbad et al., *J. Chromatography A* (2011) 1218 8897-8902; Lubbad et al., *J. Chromatography A* (2011) 1218 2362-2367). Monoliths, broadly, are any single bodied structure containing interconnected repeating cells or channels, that are characterized by a defined porosity and which support interactions between the solid and surrounding mobile phase. Mobile phases are forced through the porous monolithic media which results in convective flow and enhanced mass transfer. Monoliths may be based on polymers (i.e., organics), silica, organic-silica hybrids, inorganics, cyrogels and agarose, with the first two types being the most predominant.

Provided herein, in the broadest sense, are monoliths with attached recognition compounds and arrays thereof. In one aspect, monoliths with attached recognition compounds that selectively bind ligands are provided. In some embodiments, the monoliths are porous. In other embodiments, the monoliths include an ionizable group. In some of these embodiments, the recognition compounds are ionically attached to the monoliths. In other of these embodiments, the recognition compounds are covalently attached to the monoliths.

In some embodiments, the recognition compounds are oligonucleotides, single stranded RNA, single stranded DNA, DNA binding proteins, RNA binding proteins, peptide nucleic acids, peptides, depsipeptides, polypeptides, antibodies, peptoids, polymers, polysiloxanes, inorganic compounds of molecular weight greater that 50 daltons, organic compounds of molecular weight between about 3000 daltons and about 50 daltons or combinations thereof. In other embodiments, the ligands are oligonucleotides, single stranded RNA, single stranded DNA, DNA binding proteins, RNA binding proteins, peptide nucleic acids, peptides, depsipeptides, polypeptides, antibodies, peptoids, polymers, polysiloxanes, inorganic compounds of molecular weight greater that 50 daltons, organic compounds of molecular weight between about 3000 daltons and about 50 daltons or combinations thereof. In still other embodiments, the recognition compounds are oligonucleotides, single stranded RNA, single stranded DNA, DNA binding proteins, RNA binding proteins, peptide nucleic acids, peptides, depsipeptides, polypeptides, antibodies, peptoids, organic compounds of molecular weight between about 3000 daltons and about 50 daltons or combinations thereof and the ligands are single stranded DNA, single stranded RNA, peptides, depsipeptides, polypeptides, antibodies, peptoids, organic compounds of molecular weight between about 3000 daltons and about 50 daltons or combinations thereof.

In some embodiments, the recognition compounds are oligonucleotides, single stranded RNA, single stranded DNA, DNA binding proteins, RNA binding proteins, peptide nucleic acids or combinations thereof. In other embodiments, the ligands are single stranded DNA, single stranded RNA or combinations thereof. In still other embodiments, the recognition compounds are oligonucleotides, single stranded RNA, single stranded DNA, DNA binding proteins, RNA binding proteins, peptide nucleic acids or combinations thereof and the ligands are single stranded DNA, single stranded RNA or combinations thereof.

In some embodiments, the recognition compounds are proteinacious DNA binding proteins such as the lac repressor, trp repressor, lambda repressor, arc repressor or engineered variants of these repressors with novel DNA binding specificity and the ligands are double stranded DNA. In yet other embodiments, the recognition compounds are site specific nucleases such as CreI family meganucleases or TALEN nucleases lacking nuclease activity but retaining sequence specific DNA recognition properties.

In some embodiments, the monolith is formed from silica copolymers. In other embodiments, the silica copolymers include a monomer selected from the group consisting of

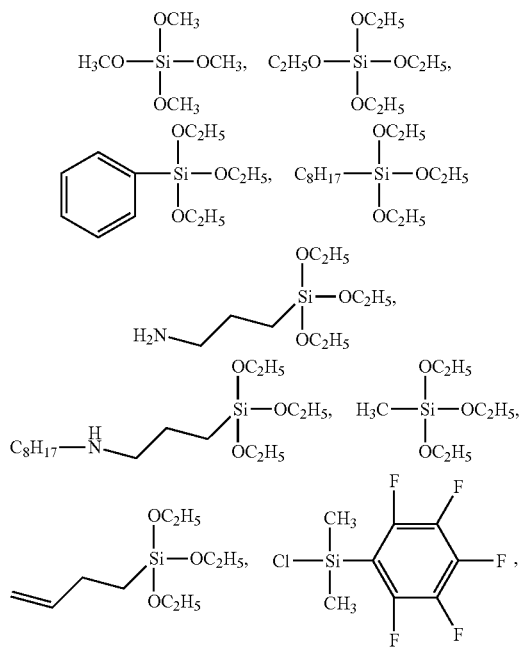

-continued

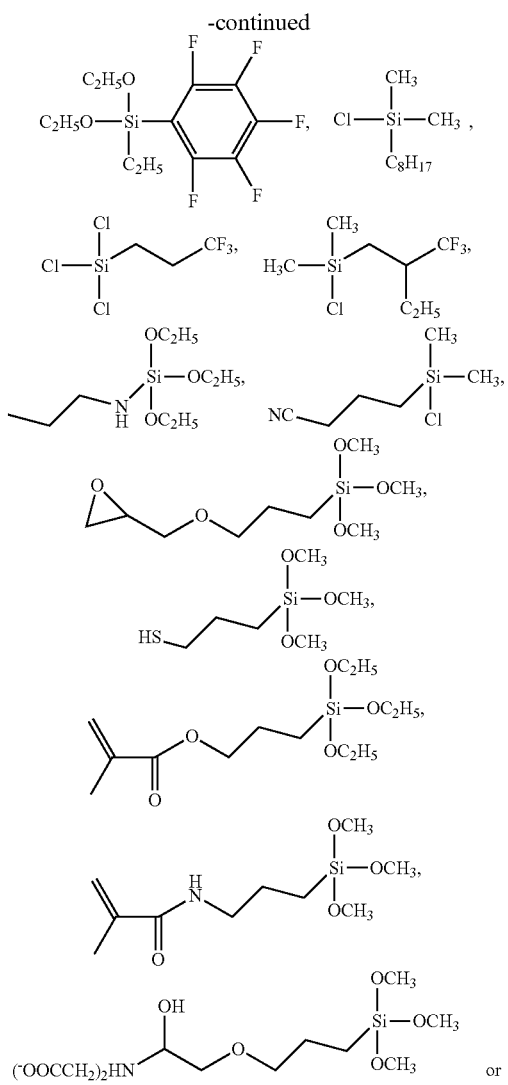

combinations thereof.

Silica based monoliths may be prepared by hydrolysis and polycondensation of alkoxysilanes, catalyzed by acid, in presence of a porogen. After heating and drying the sol-gel network may be derivatized by silation. Functional groups appropriate for attachment of recognition compounds may be introduced into the silica monolith by direct incorporation of functionalized monomers in the fabrication process or by modification of the silica monolith. For example,

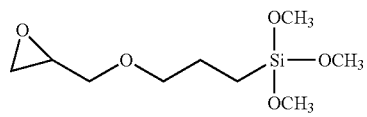 [SMILES: CO[Si](CCCOCC1CO1)(OC)OC]

may be functionalized, as described below for GMA-co-EDMA polymer monoliths. Another silica monolith that may be useful for practicing the methods described herein is poly(p-methylstyrene-co-bis(p-vinylbenzyl)dimethsilane (Wieder et al., *J. Chromatography A* (2008) 1191 252-263).

Modification of the silica monolith is usually preferable, since a change in chemical functionality does not require optimization of the physical properties of a new monolith. Here, the sol-gel monoliths are chemically modified by silation with organochlorosilane or organoalkoxysilane reagents such as some the monomers shown above. The functional groups on the silica monolith may be directly functionalized with recognition compounds, for example, by ether, ester or amide bond formation, if the recognition compound contains complementary functionality. In some embodiments, cycloaddition of complementary functional groups (e.g., azide and acetylene; diene and electron deficient olefin) or click chemistry (Evans, R. A. Australian J. of Chemistry, 60 (6): 384-395 (2007) may be used to attach the recognition compound to the monolith.

Alternatively, a bifunctional linker may be attached to the functional groups of the silica monolith and the recognition compound covalently bonded to the monolith through formation of a amide, carbamate, ester, urea, urethane, carbon-nitrogen, carbon-carbon, ether, thioether or disulfide bond with a complementary functional group on the bifunctional linker. In some embodiments, cycloaddition of complementary functional groups (e.g., azide and acetylene; diene and electron deficient olefin) or click chemistry may be used to attach the linker covalently bonded to the monolith to the recognition compound.

In addition, the recognition compounds may be functionalized with a linker, which contains functional groups capable of reacting with the functional groups on the silica monolith. As before, a recognition compound attached to a linker may be covalently bonded to the monolith through formation of an amide, carbamate, ester, urea, urethane, carbon-nitrogen, carbon-carbon, ether, thioether or disulfide bond with a complementary functional group on the linker. In some embodiments, cycloaddition of complementary functional groups (e.g., azide and acetylene; diene and electron deficient olefin) or click chemistry may be used to attach the monolith to the linker covalently bonded to the recognition compound.

In some embodiments, the monolith is an organic-inorganic silica hybrid which combines advantages of both inorganic monoliths and organic monoliths (i.e., mechanical and structural stability in organic solvent and easy functionalization). Such monoliths may be prepared from silane that has been modified to have an organic functional group as part of its structure.

In some embodiments, the monolith may be an inorganic monolith such as, for example, a zirconia, hafnia or titania monolith (Hoth et al., *J. Chromatogr. A*, (2005) 392; Randon et al., *J. Chromatogr. A*, (2006) 19; Rivera et al., *Analyst.* (2009), 31; Kubo et al., *Mater. Let.* (2010) 177; Konishi et al., *J. Chromatogr. A*, (2009) 7375). The above inorganic monoliths are resistant to extremes of pH and temperature which may be problematic with silica monoliths and often have unusual and unique selectivity. In some embodiments, inorganic monoliths may be functionalized with recognition compounds in the manner described above for silica monoliths.

Polymer based monoliths are usually highly crosslinked structures where the internal structure includes fused arrays microglobules separated by pores. The structural rigidity of porous polymer monoliths is due to the extensive crosslinking typically found in these structures.

In some embodiments, the monolith comprises organic copolymers. In other embodiments, the organic copolymer is a combination of a monovinyl polymers and a polyvinyl polymer. In still other embodiments, the organic copolymer is a combination of monovinyl polymers and polyvinyl polymers. In still other embodiments, the organic copolymer is a polyvinyl polymer or combinations of polyvinyl polymers.

In some of the above embodiments, the copolymer includes a monovinyl monomer selected from the group consisting of vinyl styrene, vinylnaphthalene, vinylanthracene and their ring substituted derivatives wherein the substituents include chloromethyl, alkyls with up to 10 carbon atoms, hydroxyl, t-butyloxycarbonyl, halogen, nitro, protected hydroxyls or amino groups, acrylamides, and methacrylamides and their derivatives substituted on the nitrogen atom with one or two $C_{1-5}$ alkyls, $C_{1-4}$ alkylamninoalkyls or dialkylaminoalkyls, $C_{1-4}$ methoxyaminoalkyls, $C_{1-4}$ dimethoxy or diethoxyaminoalkyls, $C_{1-4}$ methoxyalkyls, tetrahydropyranyl, and tetrahydrofurfuryl groups, N-acryloylpiperidine, N-acryloylpyrrolidone, and mixtures thereof, acrylic acid esters, methacrylic acid esters, alkyl acrylates, alkyl methacrylates, perfluorinated alkyl acrylates, perfluorinated alkyl methacrylates, glycidyl acrylates, glycidyl methacrylates, hydroxyalkyl acrylates, hydroxyalkyl methacrylates, wherein the alkyl group in each of the aforementioned alkyls consists of 1-10 carbon atoms, sulfoalkyl acrylates, sulfoalkyl methacrylates, oligoethyleneoxide acrylates, oligoethyleneoxide methacrylates, acrylate and methacrylate derivatives including primary, secondary, tertiary, and quarternary amine, epoxide and zwitterionic functionalities, vinyl pyridines, vinylacetate, vinylpyrrolidone, vinylazlactone or combinations thereof. In other embodiments, the monovinyl monomers include, but are not limited to, styrene, vinylnaphthalene, vinylanthracene and their ring substituted derivatives wherein the substituents include chloromethyl, alkyls with up to 18 carbon atoms, hydroxyl, t-butyloxycarbonyl, halogen, nitro, protected hydroxyls, amino groups or combinations thereof. In still other embodiments, the monovinyl monomers include but are not limited to, acrylamides, methacrylamides and their derivatives substituted on the nitrogen atom with one or two $C_{1-5}$ alkyls. $C_{1-4}$ alkylaminoalkyls or dialkylaminoalkyls, $C_{1-4}$ methoxyaminoalkyls, $C_{1-4}$ dimethoxy or diethoxyaminoalkyls, $C_{1-4}$ methoxyalkyls, tetrahydropyranyl, and tetrahydrofurfuryl groups, N-acryloylpiperidine and N-acryloylpyrrolidone or combinations thereof. In still other embodiments, the monovinyl monomer may also be selected from the group consisting of acrylic and methacrylic acid esters, alkyl acrylates, alkyl methacrylates, perfluorinated alkyl acrylates, perfluorinated alkyl methacrylates, hydroxyalkyl acrylates, hydroxyalkyl methacrylates, wherein the alkyl group in each of the aforementioned alkyls consists of 1-10 carbon atoms, sulfoalkyl acrylates, sulfoalkyl methacrylates, oligoethyleneoxide acrylates, oligoethyleneoxide methacrylates, and acrylate and methacrylate derivatives including primary, secondary, tertiary, and quarternary amine, epoxide and zwitterionic functionalities, vinylacetate, vinylpyrrolidone, vinylazlactone and combinations thereof.

In some embodiments, the copolymer includes a monovinyl monomer selected from the group consisting of

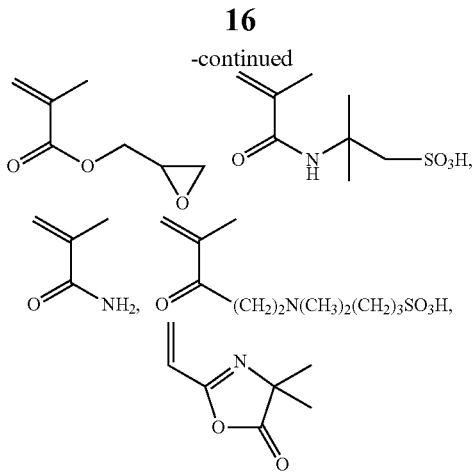

and combinations thereof.

In some embodiments, the polyvinyl monomer is an alkylene diacrylate, alkylene diacrylamide, alkylene dimethacrylate, alkylene diacrylamide, alkylene dimethacrylamide, hydroxyalkylene diacrylate, hydroxyalkylene dimethacrylate, wherein the alkylene group in each of the aforementioned alkylene monomers consists of 1-10 carbon atoms, oligoethylene glycol diacrylate, oligoethylene glycol dimethacrylate, vinyl esters of polycarboxylic acid, divinylbenzene, divinylnaphthalene, pentaerythritol dimethacrylate, pentaerythritol trimethacrylate, pentaerythritol tetramethacrylate, pentaerythritol diacrylate, pentaerythritol triacrylate, pentaerythritol tetraacrylate, trimethylopropane trimethacrylate, trimethylopropane acrylates or combinations thereof. In other embodiments, the polyvinyl monomer is selected from the group consisting of

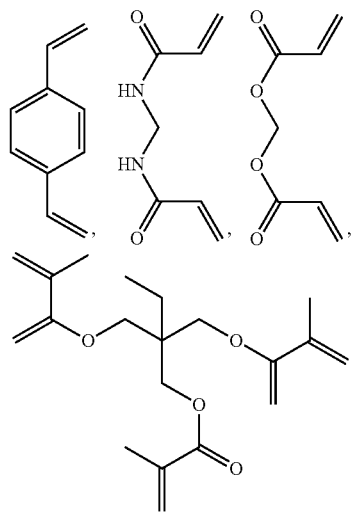

and combinations thereof.

Polymer monoliths are usually fabricated from a mixture including a free radical initiator and monomers (including at least one polyvinyl monomer) dissolved in at least one porogen. Typical porogenic solvents include common organic solvents, such as, for example, tetrahydrofuran, acetonitrile, toluene, chlorobenzene, hexane, methanol, dimethylformamide, cyclohexanol, dodecanol, supercritical $CO_2$, ether, etc. Formation of the monolith is triggered by breakdown of a initiator (e.g., AIBN, TEMPO, APS, TMED, etc.) into a free radical by an external source (e.g., photoinitiation, heat, etc.) or photoexcitation of an initiator (e.g., benzophenone) which induces the formation of polymer chains that precipitate out of the reaction mixture eventually agglomerating together to form a continuous solid structure. The morphology of the monolith is dependent on numerous variables, such as, for example, the polyvinyl monomer(s), the monovinyl monomers, temperature, the composition and percentage of the porogenic solvents (porogens), the concentration of the free radical initiator and the method used to initiate polymerization.

In some embodiments, polymer monoliths are prepared by polymerizing a mixture which includes one or more polyvinyl monomers in the presence of an initiator and a porogen. In other embodiments, polymer monoliths are prepared by polymerizing a mixture which includes one or more polyvinyl monomers in the presence of an initiator, a porogen and one or more monovinyl monomers. The mixture is usually washed with a suitable solvent to remove the porogen and other impurities.

In some embodiments, the mixture is one or more polyvinyl monomers in an amount of about 10 to about 60 vol %, about 45% to about 90 vol % porogens and between about 0.1 to about 1 vol % initiator. In other embodiments, the mixture is one or more polyvinyl monomers in an amount of about 10 to about 50 vol %, about 45% to about 85 vol % porogens and between about 0.1 to about 1 vol % initiator. In still other embodiments, the mixture is one or more polyvinyl monomers in an amount of about 20 to 40 vol %, about 45 to about 80 vol % porogens and between about 0.1 to about 1 vol % initiator. In still other embodiments, the mixture is one or more polyvinyl monomers in an amount of about 15 to 40 vol %, about 45 to about 85 vol % porogens and between about 0.1 to about 1 vol % initiator. In still other embodiments, the mixture is about 10-40% of one or more monovinyl monomers, 10 to 40 vol % of one or more polyvinyl monomers, about 20 to about 80 vol % porogens and between about 0.1 to about 1 vol % initiator. In still other embodiments, the mixture is about 20-30% of one or more monovinyl monomers, 20 to 30 vol % of one or more polyvinyl monomers, about 20 to about 60 vol % porogens and between about 0.1 to about 1 vol % initiator. In still other embodiments, the mixture is one or polyvinyl monomers in an amount of about 25 to 35 vol %, about 20 to about 75 vol % porogens and between about 0.1 to about 1 vol % initiator.

In some embodiments, the monolith is poly(GMA-co-EDMA), poly(HEMA-co-EDMA), poly(EDMA-co-MAA), poly(HEMA-co-EDMA-co-SPMA), poly(GMA-co-DEGDMA), poly(DAEM-co-PEGDA), poly(MAETA-co-PGDA), poly(HMA-co-EDMA), poly(LMA-co-EDMA), poly(BMA-co-EDMA), poly(ODMA-co-EDMA), poly(CMS-co-DVB), poly(GMA-co-DVB), poly(GMA-co-TRIM), poly(styrene-co-DVB), (NBE-co-(NBE-CH$_2$O)$_3$SiCH$_3$). In these embodiments, the above polymers are made by polymerization of GMA with EDMA, HEMA with EDMA, EDMA with MAA, HEMA with EDMA and SPMA, GMA with DEGDMA, DAEM with PEGDA, MAETA with PGDA), HMA with EDMA), LMA with EDMA, BMA with EDMA, ODMA with EDMA), CMS with DVB, GMA with DVB, GMA with TRIM and styrene with DVB, respectively.

Functional groups appropriate for attachment of recognition compounds may be introduced into the polymer monolith by direct incorporation of functionalized monomers in the fabrication process or by modification of the polymer monolith. Some examples of functionalized monomers include those illustrated below:

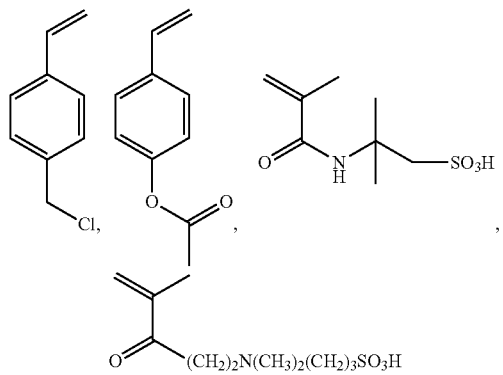

Modification of polymer monoliths is usually preferable, since a change in chemical functionality does not require optimization of the physical properties of a new monolith. Here, the polymer monoliths may be chemically modified, for example, by reaction with epoxy, chloromethyl, phenolic hydroxyls and azalactone functional groups disposed on the surface of the monolith (Luo et al., J. Chomatogr. A (2001) 926 255; Gusev et al., J. Chomatogr. A (1999) 855 273; Xie, et al., Biotechnol Bioeng. (1999) 62 30) by polymerization of functionalized monomers. The functional groups on the polymer monolith may be directly reacted with recognition compounds, for example, by ether, ester or amide bond formation, if the recognition compound contains complementary functionality.

Alternatively, a bifunctional linker may be attached to the functional groups of the polymer monolith and the recognition compound covalently bonded to the monolith through formation of a amide, carbamate, ester, urea, urethane, carbon-nitrogen, carbon-carbon, ether, thioether or disulfide bond with a complementary functional group on the bifunctional linker. In some embodiments, cycloaddition of complementary functional groups (e.g., azide and acetylene; diene and electron deficient olefin) or click chemistry may be used to attach the linker covalently bonded to the monolith to the recognition compound.

In addition, the recognition compounds may be functionalized with a linker, which contains functional groups capable of reacting with the functional groups on the polymer monolith. As before, a recognition compound attached to a linker may be covalently bonded to the monolith through formation of an amide, carbamate, ester, urea, urethane, carbon-nitrogen, carbon-carbon, ether, thioether or disulfide bond with a complementary functional group on the linker. In some embodiments, cycloaddition of complementary functional groups (e.g., azide and acetylene; diene and electron deficient olefin) or click chemistry may be used to attach the monolith to the linker covalently bonded to the recognition compound.

Useful for attachment of recognition groups to polymer monoliths are monomers which contain oxirane groups, such as, for example, GMA or derivatives thereof. Copolymers containing such monomers can be ring opened with various nucleophiles such as, for example, azide, sulfide ion, amines, etc. which can then be used to react with complementary functionality on a bifunctional linker, a linker attached to a recognition compound or a recognition compound to provide in the last two cases a recognition compound attached to a monolith. For example, poly(GMA-co-EDMA) or poly(GMA-co-DVB) after reaction with activated esters, azide, sulfide ion or amines can react with recognition compounds containing dienes, acetylenes, thiols and activated esters to provide Diels Alder adducts, 1,3 dipolar cycloadducts, disulfide and amides, respectively. Similarly, poly(CMS-co-DVB) after reaction with azide, sulfide ion or amines can react with recognition compounds containing acetylenes, thiols and activated esters to provide 1,3 dipolar cycloadducts, disulfide and amides, respectively. Poly (GMA-co-EDMA) or poly(GMA-co-DVB) can also be hydrolyzed to diols, which can then be oxidized to aldehydes. Both of the above functionalities can react with complementary functionality on a linker, a linker attached to a recognition compound or a recognition compound to provide in the last two cases a recognition compound attached to a monolith.

In some of the above embodiments, the recognition compound is a nucleic acid. In other embodiments, the recognition compound is an oligonucleotide. In exemplary embodiments, poly(GMA-co-EDMA) or poly(GMA-co-DVB) or poly(CMS-co-DVB) monolith is reacted with azide to provide a monolith containing an azide functionality. In some of these embodiments, the oligonucleotides contain a 5' alkynyl group (e.g., $C_3$-$C_{20}$) which is attached to the 5' end of the oligonucleotide with a linker (e.g., PEG or poly T). In some the above embodiments, the oligonucleotide will be linked with Cu (I) dependent click chemistry to the monolith.

In other exemplary embodiments, a poly(GMA-co-EDMA) or poly(GMA-co-DVB) or poly(CMS-co-DVB) monolith is reacted with azide to provide a monolith containing an azide group. In some of these embodiments, the oligonucleotides contain terminal alkynes, dibenzocyclooctyne or bicyclo[6.1.0]nonyne which are attached to the 5' end of the oligonucleotide with a linker (e.g., PEG or poly T). In some the above embodiments, the oligonucleotide will be linked to the monolith with Cu free click chemistry.

Free radical addition, grafting and photografting approaches may also been used to functionalize monoliths with reactive functionality by adding polymeric ligands onto the surface of the monolith (Myer et al., *Macromolecules* (2000) 3, 7769-7775; Rohr et al., *Macromolecules* (2003) 36, 1677-1684; Wang et al., *J. Chromatography A* (2007) 1147, 24-29). Such ligand containing polymers may substantially increase the density of functional groups on the monolith surface thus increasing the binding capacity of the monolith surface. The skilled artisan will appreciate that many other methods may be used to functionalize polymer monoliths and attach recognition elements to a monolith.

In some embodiments, poly(GMA-co-EDMA) or poly (GMA-co-DVB) after reaction with activated esters, azide, sulfide ion or amines are converted to ion exchange resins. In other embodiments, poly(CMS-co-DVB) after reaction with azide, sulfide ion or amines are converted to ion exchange resins. Poly (GMA-co-EDMA) or poly(GMA-co-DVB) can also be hydrolyzed to diols, which can then be oxidized to aldehydes and further converted to ion exchange resins through functional group manipulation.

In some embodiments, the porous monolith has a percent porosity of between about 45% to about 85%. In other embodiments, the porous monolith has a percent porosity of between about 60% and about 75%. In still other embodiments, the volume fraction of mesopores (5 nm-50 nm) is between about 30% and about 80%. In still other embodiments, the volume fraction of micropores (2 nm) is between about 0% and about 10%. In still other embodiments, the volume fraction of pores (50 nm-300 nm) is between about 1% and about 20%. In still other embodiments, the volume fraction of flow through pores (>300 nm) is less than about 40%.

In some embodiments, the pore size of the porous polymer monolith is in the range of between about 5 nm to about 10.000 nm. In other embodiments, the pore size of the porous polymer monolith is in the range of between about 50 nm to about 5,000 nm. In still other embodiments, the pore size of the porous polymer monolith is in the range of between about 100 nm to about 10,000 nm. In still other embodiments, the pore size of the porous polymer monolith is in the range of between about 50 nm to about 700 nm.

In still other embodiments, the average micropore size of the monolith is less than about 2 nm. In still other embodiments, the average mesopore size of the monolith is between about 2 nm and about 50 nm. In still other embodiments, the average micropore size of the monolith is less than about 2 nm, the average mesopore size of the monolith is between about 2 nm and about 50 nm and the average pore size of the monolith is between about 50 nm and about 700 nm.

In some embodiments, the specific surface area of the polymer matrix is in the range of between about 0.5 $m^2$/g to about 1000 $m^2$/g. In other embodiments, the specific surface area of the polymer matrix is in the range of between about 1 $m^2$/g to about 500 $m^2$/g. In still other embodiments, the specific surface area of the polymer matrix is in the range of between about 5 $m^2$/g to about 200 $m^2$/g. In still other embodiments, the specific surface area of the polymer matrix is in the range of between about 10 $m^2$/g to about 100 $m^2$/g. In still other embodiments, the specific surface area of the polymer matrix is in the range of between about 20 $m^2$/g to about 60 $m^2$/g. In still other embodiments, the specific surface area of the polymer matrix is in the range of between about 30 $m^2$/g to about 50 $m^2$/g.

In some embodiments, the permeability of the monolith is between about 1 millidarcy and about $1 \times 10^4$ darcy. In other embodiments, the permeability of the monolith is between about $8.9 \times 10^2$ darcy and about $8.9 \times 10^4$ darcy. In still other embodiments, the permeability of the monolith is between about 1 millidarcy and about $1 \times 10^3$ darcy. In still other embodiments, the permeability of the monolith is about $8.9 \times 10^3$ darcy.

While not desiring to be bound by theory, properties of monoliths which may be important in routing or binding ligands include rapid hybridization kinetics of large ligand macromolecules in solution to recognition elements immobilized on the monolith, low back pressure and high binding capacity of the monolith with attached recognition element for the ligand.

In some embodiments, the density of the recognition compound is between about 1 pmol/10 µl and about 1 µmol/10 µl. In still other embodiments, the density of the recognition compounds is about 1 nmol/10 µl.

In some embodiment, the recognition compounds are oligonucleotides and the ligands are single stranded DNA, single stranded RNA sequences or combinations thereof. In some of the above embodiments, the oligonucleotides have between about 10 nucleic acid subunits and about 50 nucleic acid subunits. In other of the above embodiments, the oligonucleotides have between about 15 nucleic acid subunits and about 40 nucleic acid subunits. In still other of the above embodiments, the rate constant of binding to complementary nucleic acid sequences of the recognition compounds is between about $1 \times 10^2$ $M^{-1}s^{-1}$ and about $1 \times 10^6$ $M^{-1}s^{-1}$. In still other of the above embodiments, the rate constant of binding to complementary nucleic acid sequences of the recognition compounds is between about $1\times10^3$ $M^{-1}s^{-1}$ and about $1\times10^6$ $M^{-1}s^{-1}$. In still other of the above embodiments, the rate constant of binding to complementary nucleic acid sequences of the recognition compounds is between about $1\times10^2$ $M^{-1}s^{-1}$ and about $1\times10^5$ $M^{-1}s^{-1}$. In general, the flow through monoliths, such as those describe above may be useful for rapid and specific DNA/RNA/nucleic acid hybridization. In some embodiments, the nucleic acid is not a homopolymer.

In some embodiments, the monolith is a cryogel monolith (Malik et al., *J. Sep Sci.* (2006) 1686; Galaer et al., *J. Sep Sci.* (2012) 1173; Arvidsson et al., *J. Chromatography A* (2002) 27; Daniak et al., *J. Chromatography B* (2006) 145. Cryogels are gel matrices formed in the presence moderately frozen solutions of monomeric and polymeric precursors which have exemplary chemical and physical stability. Cryogel monoliths which are typically polyacrylamide based, possess pores which are typically larger than those of other gels which make them particularly useful matrices for large entities such as protein aggregates, membrane fragments, viruses etc. In some embodiments, recognition compounds may be attached may be attached to cyrogel monoliths by the methods provided, supra.

In some embodiments, the monolith is an agarose based monolith. In other embodiments, the monolith is a superporous agarose based monolith. In some of these embodiments, the diameter of the superpore is between about 20 μm and about 200 μm. In others of these embodiments, the volume of the superpore varies between about 20% and 50%. Agarose monoliths may be prepared by casting agarose emulsions (Gustavsson et al., *J. Chromatography A*, (1999), 832 29-39; Gustavsson et al., *J. Chromatography A*, (2000), 925 69-78).

In general, monoliths derived from agarose can be functionalized with recognition compounds by reaction with the free hydroxyl groups of the alternating D-galactose and L-galactopyranose subunits of the polysaccharide. The hydroxyl groups may be directly functionalized with recognition compounds, for example, by ether, ester or carbamate bond formation if the recognition compound contains complementary functionality. Alternatively, a bifunctional linker may attached to the hydroxyl groups of the polysaccharide, and the recognition compound attached through formation of a amide, carbamate, ester, urea, urethane, carbon-nitrogen, carbon-carbon, ether, thioether or disulfide bond or by cycloaddition with an appropriate functional group on the attached linker (e.g., an azide, diene or electron deficient olefin) or click chemistry. In addition, the recognition compounds may be functionalized with a bifunctional linker, which contains a group capable of reacting with a hydroxyl compound.

In another aspect, a monolith media is provided. The monolithic media includes aggregated particles with attached recognition compounds which selectively bind ligands. By way of illustration, but without limitation, negatively charged resin particles may be grafted to provide a positively charged grafted resin particles. The positively charged grafted resin particles are then mixed with uncoated resin particles to form aggregated particles through ionic binding. Recognition compounds can be attached to aggregated particles by a variety of method know to those of skill in the art and the aggregated particles can be used to form a column. The advantage of such an approach is that covalent or non-covalent adhesion of the monolith to the wall is not necessary since packing of the aggregated particles prevents gaps between the wall surface and the monolith.

In some embodiments, a housing (e.g., a column or well) is provided. The housing encompasses one or more monoliths which include attached recognition compounds which selectively bind ligands. In some embodiments, the monolith is bonded to the housing. In some embodiments, the housing selectively binds members of compound libraries. In some of these embodiments, the library is provided by phage display, RNA display or nucleic acid programmable combinatorial chemistry. In other of these embodiments, the library comprises single stranded DNA, single stranded RNA sequences, peptides, depsipeptides, polypeptides, antibodies, peptoids, organic compounds of molecular weight between about 3000 daltons and about 50 daltons or combinations thereof.

In some embodiments, a housing (e.g., a column or well) is provided where the recognition compounds are oligonucleotides, single stranded RNA, single stranded DNA, DNA binding proteins, RNA binding proteins, peptide nucleic acids, peptides, depsipeptides, polypeptides, antibodies, peptoids, organic compounds of molecular weight between about 3000 daltons and about 50 daltons or combinations thereof and the ligands are single stranded DNA, single stranded RNA, peptides, depsipeptides, polypeptides, antibodies, peptoids, organic compounds of molecular weight between about 3000 daltons and about 50 daltons or combinations thereof. In other embodiments, the recognition compounds are oligonucleotides, single stranded RNA, single stranded DNA, DNA binding proteins, RNA binding proteins, peptide nucleic acids or combinations thereof and the ligands are single stranded DNA, single stranded RNA or combinations thereof.

In some embodiments, a housing (e.g., a column or well) is provided where the recognition compounds are oligonucleotides and the ligands are single stranded DNA, single stranded RNA sequences or combinations thereof. In some of these embodiments, the housing can bind between about 0.5 fmol/μl and about 0.4 nmol/μl of single stranded nucleic acid. In other of these embodiments, the oligonucleotides are sequence specific for the single stranded nucleic acids. In some of these embodiments, the column routes DNA libraries, which include attached ligands such as, for example, peptides, cyclic peptides, triazenes and small organic molecules.

In some embodiments, a housing (e.g., a column or well) is provided which includes a monolith with an attached oligonucleotide which selectively binds a complementary oligonucleotide operatively linked to a chemical reaction site or a ligand. In other embodiments, the oligonucleotide is between about 10 nucleic acid subunits and about 50 nucleic acid subunits. In still other embodiments, the oligonucleotide is between about 15 nucleic acid subunits and about 40 nucleic acid subunits. In still other embodiments, the rate constant of binding to the complementary oligonucleotide is between about $1\times10^2$ $M^{-1}s^{-1}$ and about $1\times10^6$ $M^{-1}s^{-1}$. In still other embodiments, the rate constant of binding to the complementary oligonucleotide is between about $1\times10^3$ $M^{-1}s^{-1}$ and about $1\times10^6$ $M^{-1}s^{-1}$. In still other embodiments, the rate constant of binding to the complementary oligonucleotide is between about $1\times10^2$ $M^{-1}s^{-1}$ and about $1\times10^5$ $M^{-1}s^{-1}$. In still other embodiments, the complementary oligonucleotide is operatively linked to a ligand including a chemical reaction site, where the ligand is a peptide, a peptoid, an organic compound of molecular weight of less than 2000 daltons.

In some embodiments, the permeability of the monolith is between about 1 millidarcy and about $1\times10^4$ darcy. In other embodiments, the permeability of the monolith is between about 1 millidarcy and about $1\times10^3$ darcy. In still other embodiments, the permeability of the monolith is between about $8.9\times10^2$ darcy and about $8.9\times10^4$ darcy. In still other embodiments, the permeability of the monolith is about $8.9\times10^3$ darcy. In still other embodiments, the column binds the complementary oligonucleotide preparatively. In still other embodiments, the column binds between about 0.5 fmol/µl and between about 0.4 nmol/µl of the complementary oligonucleotide. In still other embodiments, the oligonucleotide is attached to the monolith by cycloaddition of an azide group on the monolith with an alkyne group operatively linked to the oligonucleotide to form a 1, 2, 3 triazole.

In some embodiments, an array including two or more columns which include a monolith with an attached oligonucleotide which selectively binds a complementary oligonucleotide operatively linked to a chemical reaction site or a ligand is provided where the complementary nucleotide is a component of a mixture. In other embodiments, the array is a block including two or more wells, where each well includes a different column. In other embodiments, columns are attached to the surface(s) of the wells. In still other embodiments, the columns are covalently attached to the surface of the wells by formation of an amide, ester, urea, urethane, carbon-silicon, carbon-nitrogen, carbon-carbon, ether, thioether, or disulfide bond or by cycloaddition. In still other embodiments, the block is comprised of titanium, aluminum, stainless steel, doped metals, glass, quartz, polycarbonate, fused silica, poly(methyl methacrylate), plastics, polyether ether ketone, doped polyether ether ketone, doped polystyrene, cyclic olefin copolymer, ultempolyetheriimide, doped polypropylene or combinations thereof. In still other embodiments, the inner wall of the block is modified to increase the surface area of the wall. In still other embodiments, the wells are abraded. In still other embodiments, the wells are threaded. In still other embodiments, the dimensions of the well are about 3.5 to 4 mm inner diameter and about 1 to 4 mm in height. In still other embodiments, the wells are addressable.

In some embodiments, an array is provided which includes a block with two or more wells. In some embodiments, the wells contain the housings which include attached recognition compounds which selectively bind ligands. In other embodiments, the monoliths are attached to the surfaces of the wells. The monoliths may be covalently attached to the surface of the well by formation of an amide, ester, urea, urethane, carbon-silicon, carbon-nitrogen, carbon-carbon, ether, thioether, or disulfide bond to the well surface. Alternatively, click chemistry or cycloaddition may provide a cycloadduct between appropriate functionality on the well surface and groups on the monolith. Functionality may be attached to the well surface, for example, by silation of the well surface with a functionalized silane compound (e.g., 3-trimethoxysilyl)propylmethacrylate) or by ionic attachment of methacryloyloxydecyldihyrogen phosphate. Alternatively the well surface may be coated with a polymer (e.g., poly(methyl methacrylate), polydimethylsiloxane, polyethylene, polypropylene, poly-2-notrborene-co-ethylene) and attached to the monolith via free radical addition, initiated, for example, by irradiation of benzophenone. In other embodiments, polyvinyl monomers may be attached to polymer coated well surfaces during monolith formation and may further react with pendant olefins on the monolith surface to covalently bond the monolith to the well surface. In still other embodiments, the monoliths may be directly attached to the well.

In some embodiments, the block comprises titanium, aluminum, stainless steel, doped metals, glass, quartz, polycarbonate, fused silica, poly(methyl methacrylate), plastics, polyether ether ketone, doped polyether ether ketone, doped polystyrene, ultempolyetheriimide, cyclic olefin copolymer, doped polypropylene or combinations thereof. The wells of the block may be modified to increase the surface area of the wall by abrasion, threading or other methods known to the skilled artisan. In some embodiments, the dimensions of the well are between about 0.1 mm and about 50 mm diameter and between about 0.1 mm height and about 10 mm height. In other embodiments, the dimensions of the well are about 10 mm diameter and about 10 mm height. In still other embodiments, the dimensions of the well are about 3.5 to about 4 mm inner diameter and about 1 to about 4 mm height. In some embodiments, the wells are addressable.

In some embodiments an array with two or more ion exchange housings (e.g., a column or well) is provided which includes filter plates or any other type of microplates or devices which allow for flow through of the mobile phase. In some of these embodiments, the ion exchange housing includes a monolith with an ionizable group. In some of these embodiments, the ionizable group is an amine, a carboxylic acid or a sulfonic acid. In some of these embodiments, the monolith is the reaction product of a copolymer which includes glycidyl methacrylate with an amine or a sulfonic acid equivalent. In other of these embodiments, the monolith is the reaction product of poly(GMA-co-EDMA), poly(GMA-co-DEGDMA) or poly(GMA-co-DVB) with an amine or sulfonic acid equivalent. In still other of these embodiments, the monolith is the reaction product of poly (CMS-co-DVB) with an amine or sulfonic acid equivalent. In some embodiments, the ion exchange column includes conventional ion exchange material.

In some embodiments, an array is provided which includes filter plates or any other type of microplates or devices which allow for flow through of the mobile phase. The array also includes a block with two or more wells. Each well contains ion exchange material. In some embodiments, the ion exchange material includes a monolith with an ionizable group. In some of these embodiments, the ionizable group is an amine, a carboxylic acid or a sulfonic acid. In some of these embodiments, the monolith is the reaction product of a copolymer which includes glycidyl methacrylate with an amine or a sulfonic acid equivalent. In other of these embodiments, the monolith is the reaction product of poly(GMA-co-EDMA), poly(GMA-co-DEGDMA) or poly (GMA-co-DVB) with an amine or sulfonic acid equivalent. In still other of these embodiments, the monolith is the reaction product of poly(CMS-co-DVB) with an amine or sulfonic acid equivalent. In some embodiments, the ion exchange material is conventional ion exchange material.

In some embodiments, the columns are attached to the surface(s) of the wells. In other embodiments, the columns are covalently attached to the surface of the wells by formation of an amide, ester, urea, urethane, carbon-silicon, carbon-nitrogen, carbon-carbon, ether, thioether, or disulfide bond or by cycloaddition.

In some embodiments, the block includes titanium, aluminum, stainless steel, doped metals, glass, quartz, polycarbonate, fused silica, poly(methyl methacrylate), plastics, polyether ether ketone, doped polyether ether ketone, doped polystyrene, cyclic olefin copolymer, ultempolyetheriimide, glass fiber filterplates, doped polypropylene or combinations thereof.

In some embodiments, the dimensions of the well are between about 0.1 mm and about 50 mm diameter and between about 0.1 mm height and about 10 mm height. In other embodiments, the dimensions of the well are about 10 mm diameter and about 10 mm height. In still other embodiments, the dimensions of the well are about 3.5 to 4 mm inner diameter and about 1 to 4 mm height. In some embodiments, the wells are addressable.

Methods of Using Monoliths with Attached Recognition Compounds and Arrays Thereof A method for preparing a nucleic acid programmed library of chemical compounds is provided. The method encompasses the steps of contacting a mixture of nucleic acid molecules with an array which includes a block which has two or more addressable wells. Each well includes a monolith with one or more attached recognition compounds which selectively bind single stranded nucleic acids thereby splitting the nucleic acid molecules into subpopulations. In some embodiments, the array includes two or oligonucleotides where the attached oligonucleotide of each column selectively binds the complementary oligonucleotide operatively linked to a chemical reaction site or a ligand, where the complementary nucleotide is a component of a mixture.

The subpopulations of nucleic acid molecules may optionally be dissociated from the recognition compounds using, for example, elevated temperature, change in ionic strength or change in pH with the dissociated nucleic acid molecules transferred to separate containers. The separated subpopulations of nucleic acid molecules are then reacted with different chemical subunits, where the nucleic acid molecules include at least one binding sequence and one chemical reaction site which are operatively linked. When the subpopulations of nucleic acid molecules are optionally transferred to separate containers the wells which include monoliths with attached recognition compounds which selectively bind nucleic acids are aligned in addressable manner with the separate containers. In some embodiments, the separated subpopulations of nucleic acid molecules are immobilized prior to reaction with different chemical subunits. In other embodiments, the separated subpopulations of nucleic acid molecules are immobilized on anion exchange columns prior to reaction with different chemical subunits. In still other embodiments, the anion exchange columns include a monolith with an ion exchange group.

Another method for preparing a nucleic acid programmed library of chemical compounds is provided. The method encompasses the steps of contacting a mixture of nucleic acid molecules with an array which includes a block which has two or more addressable wells. Each well includes a monolith with one or more attached recognition compounds which selectively bind single stranded nucleic acids thereby splitting the nucleic acid molecules into subpopulations. In some embodiments, the array includes two or oligonucleotides where the attached oligonucleotide of each column selectively binds the complementary oligonucleotide operatively linked to a chemical reaction site or a ligand, where the complementary nucleotide is a component of a mixture.

The subpopulations of nucleic acid molecules is transferred to a second array which includes filter plates or any other type of microplates or devices which allow for flow through of the mobile phase and a block containing two or more addressable wells. The subpopulations of nucleic acid molecules may be dissociated from the recognition compounds, for example, using elevated temperature change ionic strength or change in pH. The wells of the second array include anion exchange material which non-specifically immobilizes the subpopulations of nucleic acid molecules. The immobilized subpopulations of nucleic acid molecules are reacted with different chemical subunits. The wells which include monoliths with one or more attached recognition compounds which selectively bind nucleic acids are aligned in addressable manner with the wells including the anion exchange material. The nucleic acid molecules include at least one binding sequence and one chemical reaction site which are operatively linked. In some embodiments, the anion exchange material includes a monolith with anion exchange groups. In some embodiments, the array includes two or more oligonucleotides where the attached oligonucleotide of each column selectively binds the complementary oligonucleotide operatively linked to a chemical reaction site or a ligand, where the complementary nucleotide is a component of a mixture. In other embodiments, the anion exchange material includes a monolith column with an ion exchange group. In other embodiments, the separated subpopulations of nucleic acid molecules are immobilized prior to reaction with different chemical subunits. In still other embodiments, the separated subpopulations of nucleic acid molecules are immobilized on anion exchange material prior to reaction with different chemical subunits.

As such, the above disclosure represents novel methods for performing DNA-programmed combinatorial chemistry ("DPCC") (see e.g., Wrenn et al., *J. Am. Chem. Soc.* (2007) 129(43) 13137-13143; Wrenn et al., *Annu. Rev. Biochem.* (2007) 76, 331-349; Harbury et al., U.S. Pat. No. 7,479,472; Harbury et al., U.S. Patent Application No. US2006/0099626) which is described below.

DPCC provides methods for synthesizing, screening, and amplifying a nucleic acid-templated combinatorial chemical library. The combinatorial chemical library comprise a plurality of species of bifunctional molecules (i.e., nucleic acid tagged molecules) that each comprise a different chemical compound moiety and a unique identifier nucleic acid sequence moiety (i.e., nucleic acid tag), wherein the nucleic acid sequence defines and directs the synthesis of the corresponding chemical compound moiety. Details of the nucleic acid tagged molecules used and traditional strategies for synthesizing and screening combinatorial nucleic acid tagged compounds are described in the references above.

Described below in greater detail are nucleic-acid tagged molecules used for producing small-molecule combinatorial libraries. Nucleic acid tagged molecules are tagged compounds having a nucleic acid tag containing at least one, typically two or more different catenated hybridization sequences and an attached, typically a covalently attached, chemical reaction moiety (FIG. 1). The hybridization sequences in any given nucleic acid tag generally differ from the sequences in any other nucleic acid tag. It should be noted that different nucleic acid tags can share a common codon. The hybridization sequences of each nucleic acid tag identify the particular chemical monomers that will be used in each successive synthesis step for synthesizing a unique chemical compound attached to the chemical reaction site. As such, hybridization sequences of each nucleic acid tag also identify the order of attachment of the particular chemical monomers to the chemical reaction site.

In general, each hybridization sequence of the nucleic acid tag provides a separate sequence for hybridizing to a complementary capture nucleic acid sequence attached to a monolith. The different hybridization sequences of the nucleic acid tags allow for sequence-specific splitting of a population of nucleic acid tagged molecules into a plurality of sub-populations of distinct nucleic acid tagged molecules. Each sub-population of nucleic acid tagged molecules is then reacted with distinct chemical monomer to allow for coupling of the distinct chemical monomer at the chemical reaction site of each nucleic acid tag.

In some embodiments, a set of orthogonal 20-mers (see orthogonal rule below) that contain BsaI site and have $T_m$ in the 57-60° C. range are selected. The above are the constant regions and there are 22 such oligos. The set above is used as a seed to generate a set of orthogonal 20-mers that have $T_m$ in the 49-53 range to be used as codons. Orthogonality between a query and the subject (sequence in seed) is defined by the following criteria: (a) in-register alignment (query nucleotide 1 matched with subject nucleotide 1) should have no more than 12 nucleotide s matching; (b) contiguous runs of not more than 9 nucleotides should match between query and subject (any register); (c) contiguous runs of not more than 6 nucleotides matching between query and subject at either the 3' or 5' end; and (4) all above conditions must be fulfilled by the reverse complement of the query.

The set of 20-mers is generated by the following rules: (a) calculating $T_m$ using nearest neighbor method; (b) discard if not in range (49-53 for codons; 57-61 for constant regions); (c) no palindromes >4 bps; and (d) no runs of a single base >4 nts.

Figure 3A:
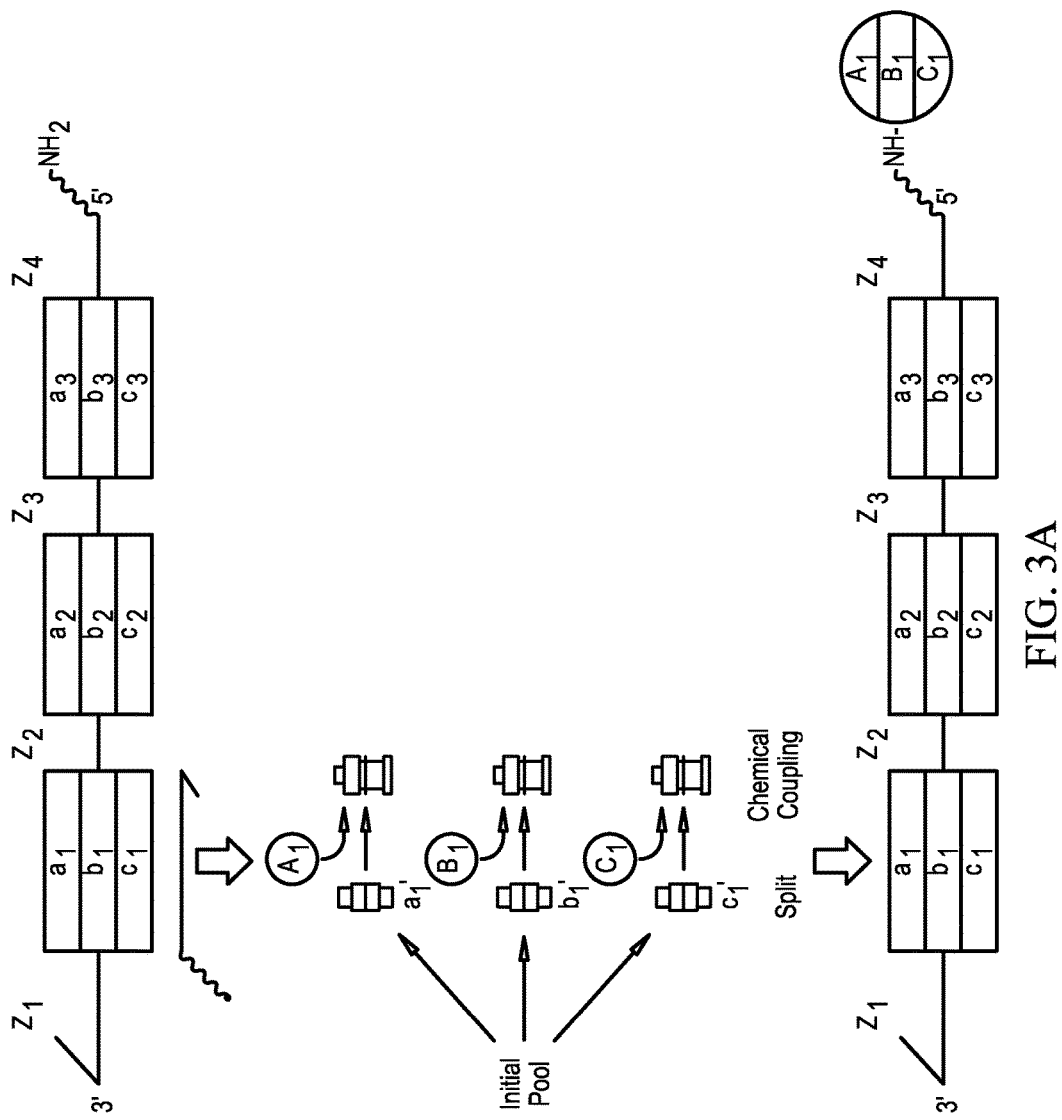
FIGS. 3A-3D illustrate a method of partition based chemical synthesis using a series of columns to generate a library of distinct chemical compounds.

To carry out a first reaction step, the population of nucleic acid tags is "split" into a plurality of sub-populations of distinct nucleic acid tags, e.g., 10 different sub-populations corresponding to the ten different hybridization sequences at the "first" position ($V_1$, e.g., $a_1$, $b_1$, or $c_1$) in each tag (FIG. 3A, top and middle panels). This is done by contacting the nucleic acid tag-containing molecules with a first group of monoliths with attached capture nucleic acids with sequences complementary to one of the different "first-position" hybridization sequences in the nucleic acid tags (e.g. $a_1'$, $b_1'$, or $c_1'$). These immobilized nucleic acids are sometimes referred to herein as "capture nucleic acid" or "capture oligonucleotides", and the sequences complementary to a nucleic acid tag sequence referred to as "capture sequences". This contacting step provides for dividing a population of molecules having different nucleic acid tags into $X_1$ sub-populations (where X represents the number of different capture sequences used to separate the pooled compounds), where each sub-population of molecules shares at least one common hybridization sequence within the nucleic acid tag.

Figure 2:
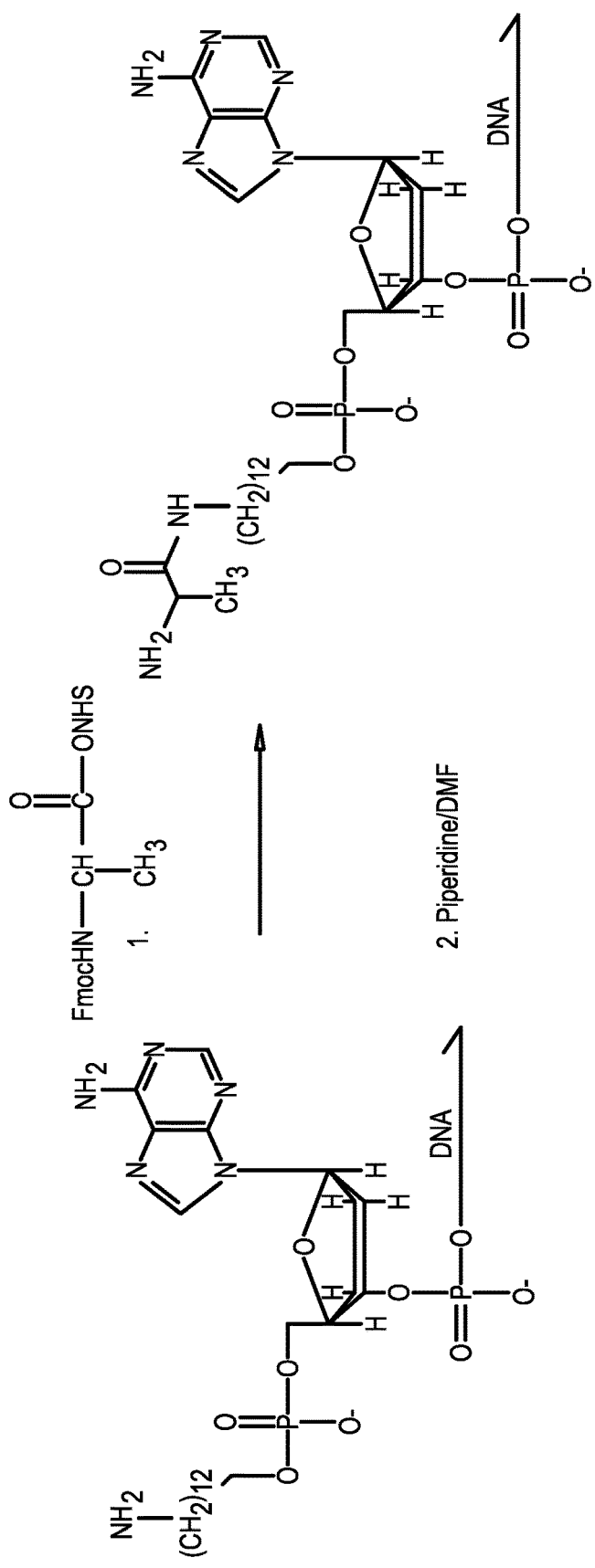
FIG. 2 shows an exemplary chemical coupling reaction at the chemical reaction site of a nucleic acid tag. A nucleic acid tag comprising a chemical reaction site is treated with the NHS ester of FMOC-alanine in DMF. The FMOC protecting group is removed with piperidine to provide an alanine coupled to the chemical reaction site of the nucleic acid tag. The process can be repeated many times, and with a variety of amino acids at successive steps in order to produce a library of distinct polypeptides.

After the first splitting step, the $X_1$ different nucleic acid tag sub-populations. (e.g., ten different sub-populations of nucleic acid tags as exemplified in FIG. 3A) are reacted with $X_1$ different chemical monomers (FIG. 3A, middle panel). The reactions are performed such that the identity of each chemical monomer used in the coupling step is directed by the particular "first" position hybridization sequence of the nucleic acid tag in the sub-population. As exemplified in FIG. 3A, the chemical monomer $A_1$, $B_1$, or $C_1$ corresponds to the particular nucleic acid tag hybridization sequence in the "first" position (e.g., $a_1$, $b_1$, or $c_1$). The first chemical coupling step converts the chemical reaction site in each tag to a reagent-specific compound intermediate, by conjugating the particular chemical monomer to the chemical reaction site of each nucleic acid tag sub-population (e.g., $A_1$, $B_1$, or $C_1$, as exemplified in FIG. 2). The result is $X_1$ different sub-populations of compounds having nucleic acid tags, each sub-population having a different chemical monomer conjugated to the chemical reaction site of each nucleic acid tag sub-population (FIG. 3A, bottom panel). For example, three different populations of nucleic acid tags (as separated by hybridization to $a_1$, $b_1$, or $c_1$ in the "split" step) are represented in the bottom panel of FIG. 3A, where a first sub-population of molecules separated by sequence is modified to contain the chemical monomer $A_1$, a second sub-population of molecules separated by the $b_1$ sequence is modified to contain the chemical monomer $B_1$, and a third sub-population of molecules separated by sequence is modified to contain the chemical monomer $C_1$. In each instance, a chemical monomer is coupled to the chemical reaction site of the nucleic acid tag-containing compound, where the added chemical monomer provides the reaction site for coupling of an additional monomer in a subsequent step as desired.

Figure 3B:
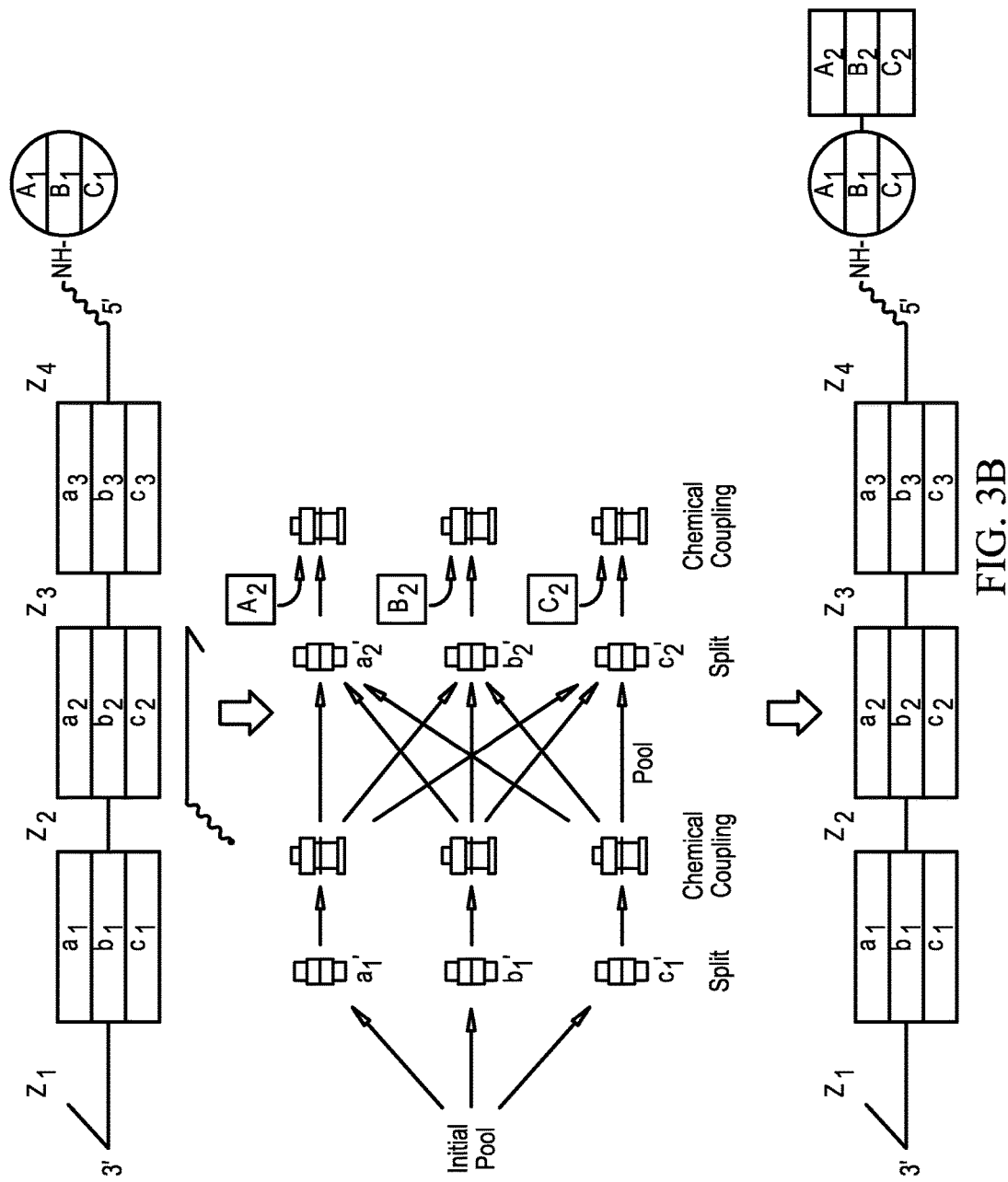

Following the first splitting and chemical coupling steps, the $X_1$ different nucleic acid tag-containing compound sub-populations are pooled and contacted with a second group of solid-phase reagents (immobilized capture nucleic acid sequences, e.g., $a_2'$, $b_2'$, or $c_2'$), each having a sequence that is complementary to one of the $X_2$ different "second-position" hybridization sequences of the nucleic acid tags (e.g., $a_2$, $b_2$, or $c_2$) (FIG. 3B, top and middle panels). As a result, the pooled population of nucleic acid tagged compounds is split into a plurality of $X_2$ sub-populations of distinct nucleic acid tags. The number of sub-populations in the second step ($X_2$) may be the same or different than the number of sub-populations resulting from the first stage split ($X_1$). As above, each sub-population of nucleic acid tagged molecules is determined by the "second-position" hybridization sequence of the nucleic acid tags (e.g., $a_2$, $b_2$, or $c_2$) (FIG. 3B, middle panel).

Each of the different "second-position" sub-populations of nucleic acid tagged compounds is then reacted with one of a second plurality of chemical monomers, a different chemical monomer for each subset (e.g., $A_2$, $B_2$, or $C_2$) (FIG. 3B, middle panel). The result is a $X_2$ different sub-populations of nucleic acid tags, each population having a different chemical monomer conjugated to the previous chemical monomer of each nucleic acid tag-containing sub-population of molecules (FIG. 3B, bottom panel). For example, as exemplified in the bottom panel of FIG. 3B, nine different sub-populations of nucleic acid tag-containing compounds can be generated, where a first population comprises the chemical monomers $A_1$ and $A_2$, a second population comprises the chemical monomers $A_1$ and $B_2$, a third population comprises the chemical monomers $A_1$ and $C_2$, a fourth population comprises the chemical monomers $B_1$ and $A_2$, a fifth population comprises the chemical monomers $B_1$ and $B_2$, a sixth population comprises the chemical monomers $B_1$ and $C_2$, a seventh population comprises the chemical monomers $C_1$ and $A_2$, an eighth population comprises the chemical monomers $C_1$ and $B_2$, and a ninth population comprises the chemical monomers $C_1$ and $C_2$.

Figure 3C:
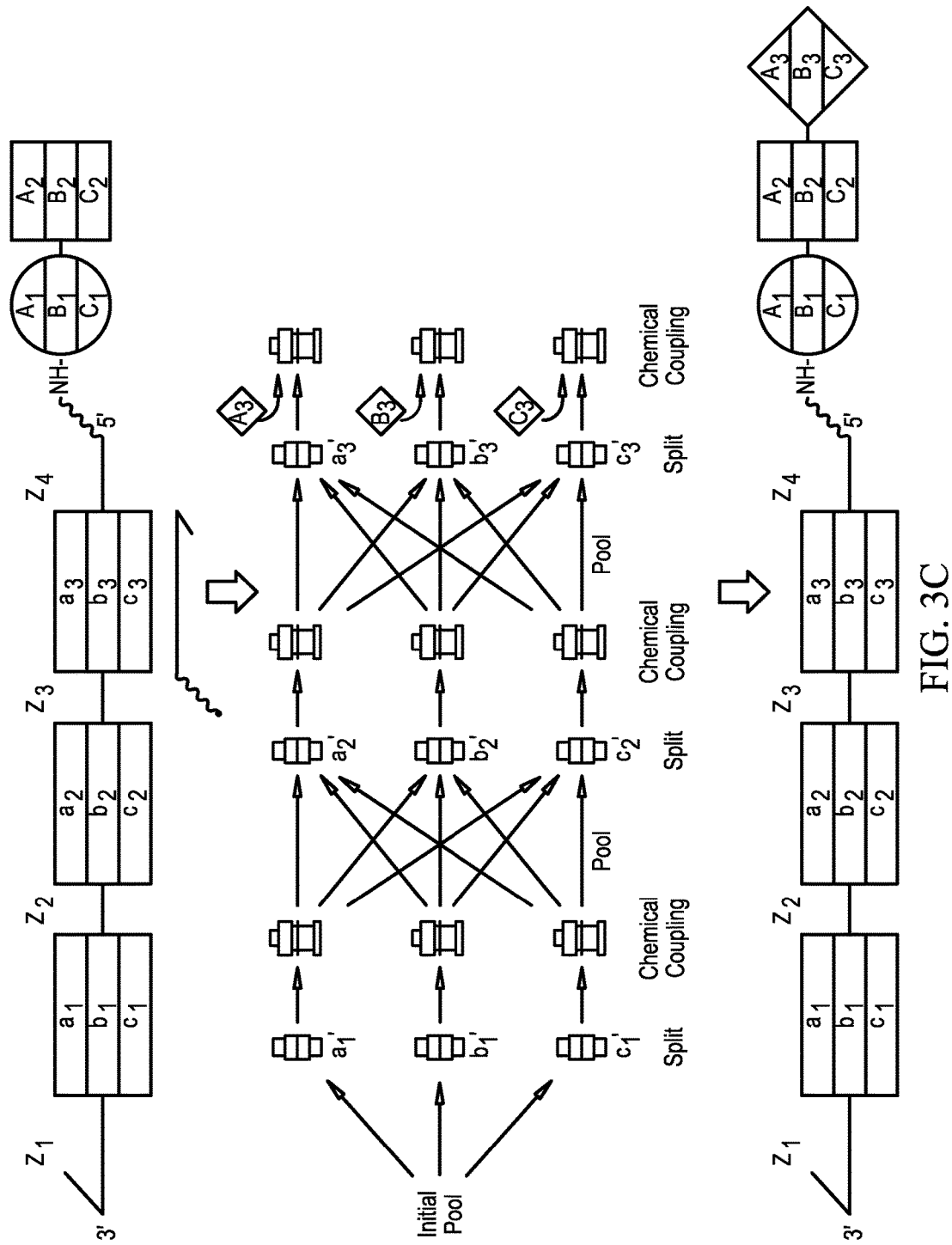
Figure 3D:
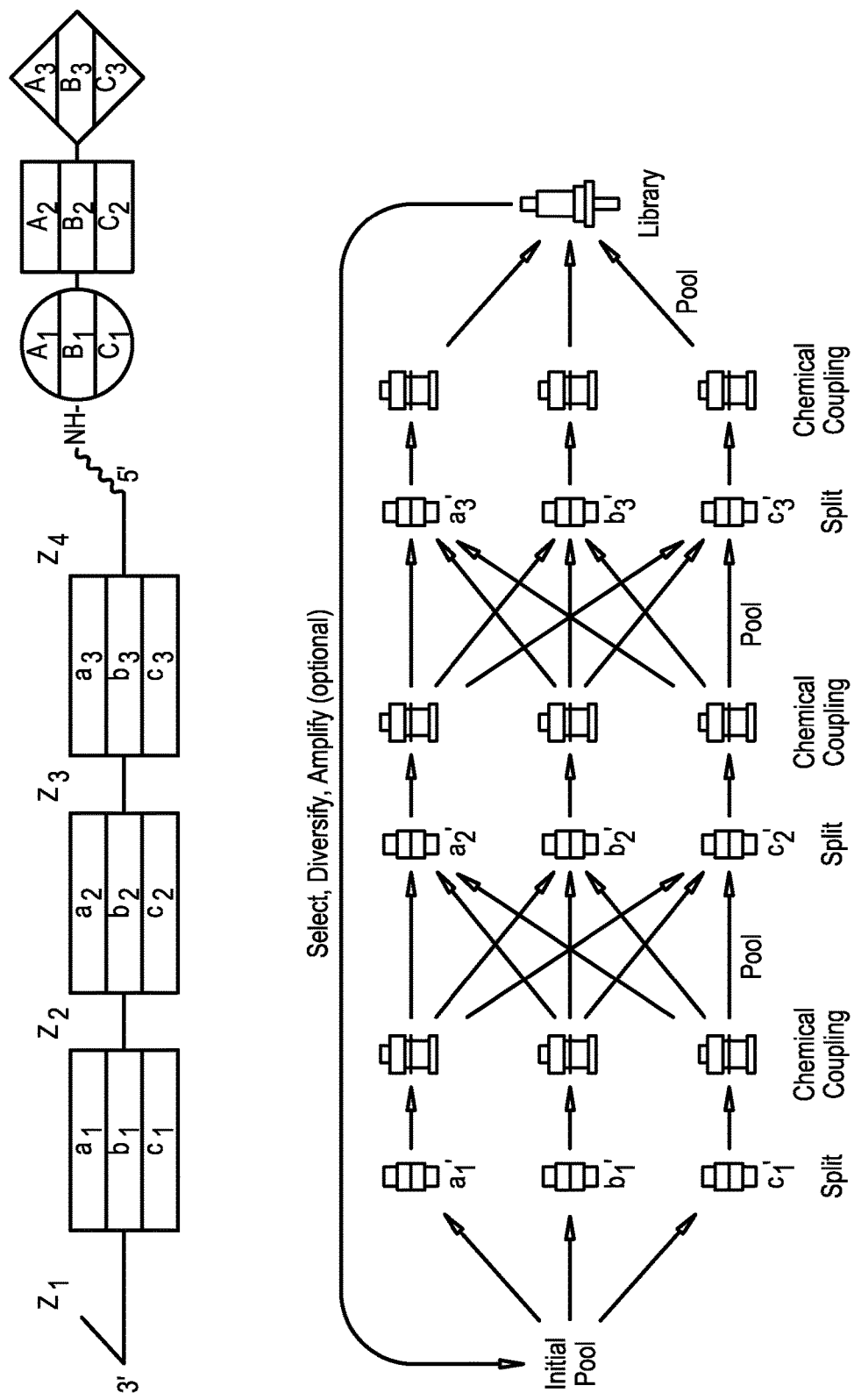

This process of splitting the previously reacted nucleic acid tags into $X_n$ different sub-population (where X represents the number of different capture sequences used to separate the pooled compounds and n represents the step number of the synthetic scheme) can be repeated as desired. For example, as illustrated in FIGS. 3C and 3D, the nucleic acid tag-containing compounds can be hybridized with a new set of immobilized capture oligonucleotides, then reacting the $X_n$ separated sub-populations of tags with $X_n$ different selected chemical monomers. These steps can be repeated until all of the desired reaction steps are performed successively on the reaction sites of the nucleic acid tag-containing compound are complete (FIG. 3C and FIG. 3D). The result is a combinatorial library of $X_1 \times X_2 \times \ldots \times X_N$ different nucleic acid tagged chemical compounds, wherein the particular of hybridization sequences at the N positions (e.g., $V_1$, $V_2$, and $V_3$, see FIG. 1) of the nucleic acid tag of each compound dictates the sequence of chemical monomers of the particular compound.

As exemplified in the top panel of FIG. 3D, twenty-seven different populations of nucleic acid tagged compounds can be generated from the steps as exemplified in FIGS. 3A-3C. The exemplary combinatorial library of compounds includes, for example, a first population comprising the chemical monomers $A_1$, $A_2$, and $A_3$, a second population comprising the chemical monomers $A_1$, $B_2$, and $A_3$, a third population comprising the chemical monomers $A_1$, $C_2$, and $A_3$, a fourth population comprising the chemical monomers $B_1$, $A_2$, and $A_3$, a fifth population comprising the chemical monomers $B_1$, $B_2$, and $A_3$, a sixth population comprising the chemical monomers $B_1$, $C_2$, and $A_3$, a seventh population comprising the chemical monomers $C_1$, $A_2$, and $A_3$, an eighth population comprising the chemical monomers $C_1$, $B_2$, and $A_3$, and a ninth population comprising the chemical monomers $C_1$, $C_2$, and $A_3$, etc.

As exemplified in FIG. 1, the nucleic acid tag is composed of $Z_n$ (e.g., n=9) regions of different catenated nucleic acid sequences and a chemical reaction site. Five of these regions are denoted $C_1$ through $C_5$ and refer to the "constant" or "spacer" sequences that are the same for the nucleic acid tags. The four remaining Z regions are denoted $V_1$ through $V_4$ and refer to the "variable" hybridization sequences at the first through fourth positions. In representative embodiments, the V regions and C regions alternate in order from the 3' end of the nucleic acid tag to the 5' end of the nucleic acid tag. In certain embodiments, the first Z region is a C region. In other embodiments, the first Z region is a V region. In certain embodiments, the last Z region is a C region. In other embodiments, the last Z region is a V region.

The variable hybridization sequences are generally different for each group of sub-population of nucleic acid tags at each position. In this embodiment, every V region is bordered by two different C regions. As will be appreciated from below, all of the V-region sequences are orthogonal, such that no two V-region sequences cross-hybridize with each other. For example, in an embodiment that comprises nucleic acid tags that include four variable regions and 400 different nucleic acid sequences for each of the four variable regions, there are a total of 1,600 orthogonal nucleic acid hybridization sequences. Such hybridization sequences can be designed according to known methods. For example, where each variable hybridization sequence comprises 20 nucleotides, with a possibility of one of four nucleotides at each position, $4^{20}$ different sequences are possible. Of the different possible candidates, specific sequences can be elected such that each sequence differs from another sequence by at least 2 to 3, or more, different internal nucleotides.

In general suitable C and V regions comprise from about 10 nucleotides to about 30 nucleotides in length, or more. In certain embodiments, C and V regions comprise from about 11 nucleotides to about 29 nucleotides in length, including from about 12 to about 28, from about 13 to about 27, from about 14 to about 26, from about 14 to about 25, from about 15 to about 24, from about 16 to about 23, from about 17 to about 22, from about 18 to about 21, from about 19 to about 20 nucleotides in length. In representative embodiments C and V regions comprise about 20 nucleotides in length.

A nucleic acid tag can comprise from about 1 to about 100 or more different V regions (hybridization sequences), including about 200, about 300, about 500, or more different V regions. In representative embodiments, a nucleic acid tag comprises from about 1 to about 50 different V regions, including about 2 to about 48, about 3 to about 46, about 4 to about 44, about 5 to about 42, about 6 to about 40, about 7 to about 38, about 8 to about 36, about 9 to about 34, about 10 to about 32, about 11 to about 30, about 12 to about 29, about 13 to about 28, about 13 to about 28, about 14 to about 27, about 15 to about 26, about 16 to about 25, about 17 to about 24, about 18 to about 23, about 19 to about 22, about 20 to about 21 different V regions.

A nucleic acid tag can comprise from about 1 to about 100) or more different C regions (constant sequences), including about 200, about 300, about 500, or more different C regions. In representative embodiments, a nucleic acid tag comprises from about 1 to about 50 different C regions, including about 2 to about 48, about 3 to about 46, about 4 to about 44, about 5 to about 42, about 6 to about 40, about 7 to about 38, about 8 to about 36, about 9 to about 34, about 10 to about 32, about 11 to about 30, about 12 to about 29, about 13 to about 28, about 13 to about 28, about 14 to about 27, about 15 to about 26, about 16 to about 25, about 17 to about 24, about 18 to about 23, about 19 to about 22, about 20 to about 21 different C regions.

The nucleic acid tags are synthesized such that regions $Z_1$ though $Z_n$ (e.g., n=9) are linked to each other beginning with $Z_1$ at the 3' and continuing in order with the chemical reaction site at the 5' end following $Z_n$. For example, beginning with the 3' end of the nucleic acid tag, $Z_1$ is linked to $Z_2$, $Z_2$ is linked to $Z_3$, $Z_3$ is linked to $Z_4$, etc., and chemical reaction site is linked to Z at any site on the nucleic acid tag, including the 3' terminus, the 5' terminus, or any other position on the nucleic acid tag.

As noted above, a population of nucleic acid tags is degenerate, i.e., almost all of the nucleic acid tags differ from one another in nucleotide sequence. The nucleotide differences between different nucleic acid tags reside entirely in the hybridization sequences (V regions). For example, an initial population of nucleic acid tags can comprise of 400 first sub-populations of nucleic acid tags based on the particular sequence of $V_1$ of each sub-population. As such, the $V_1$ region of each sub-population comprises of any one of 400 different 20 base-pair hybridization sequences. Separation of such a population of nucleic acid tags based on $V_1$ would result in 400 different sub-populations of nucleic acid tags. Likewise, the same initial population of nucleic acid tags can also comprise of 400 second subpopulations of nucleic acid tags based on the particular sequence of $V_2$ of each subpopulation, wherein the second sub-populations are different than the first subpopulations.

In the exemplary population of nucleic acid tags demonstrated in FIG. 1, the first few of the first hybridization sequences are denoted as $a_1$, $b_1$, $c_1$ . . . $j_1$, in the $V_1$ region of the different nucleic acid tags. Likewise, the first few of the second hybridization sequences are denoted as $a_2$, $b_2$, $c_2$ . . . $j_2$, in the $V_2$ region of the different nucleic acid tags. The first few of the third hybridization sequences are denoted as $a_3$, $b_3$, $c_3$ . . . $j_3$, in the $V_3$, etc.

In certain embodiments, the nucleic acid tags share the same twenty base-pair sequence for designated spacer regions while having a different twenty base-pair sequence between different spacer regions. For example, the nucleic acid tags comprise the same $C_1$ spacer region, the same $C_2$ spacer region, and the same $C_3$ spacer region, wherein $C_1$, $C_2$, and $C_3$ are different from one another.

Thus each 180 nucleotide long nucleic acid tag consists of an ordered assembly of 9 different twenty base-pair regions comprising the 4 variable regions ($a_1$, $b_1$, $c_1$ . . . $d_5$, $e_5$, $f_5$, . . . $h_{10}$, $i_{10}$, $j_{10}$) and the 5 spacer regions ($z_1$ . . . $z_{11}$) in alternating order. The twenty base-pair regions have the following properties: (i) micromolar concentrations of all the region sequences hybridize to their complementary DNA sequences efficiently in solution at a specified temperature designated Tm, and (ii) the region sequences are orthogonal to each other with respect to hybridization, meaning that none of the region sequences cross-hybridizes efficiently with another of the region sequences, or with the complement to any of the other region sequences, at the temperature Tm.

The degenerate nucleic acid tags can be assembled from their constituent building blocks by the primerless PCR assembly method described by Stemmer et al., *Gene* (1995) 164(1) 49-53 or by ligation strategies.

As noted above the nucleic acid tags further comprise a chemical reaction site, including the 3' terminus, the 5' terminus, or any other position on the nucleic acid tag. In some embodiments, the chemical reaction site can be added by modifying the 5' alcohol of the 5' base of the nucleic acid tag with a commercially available reagent which introduces a phosphate group tethered to a linear spacer, e.g., a 12-carbon chain terminated with a primary amine group (e.g., as available from Glen Research, or numerous other reagents which are available for introducing thiols or other chemical reaction sites into synthetic DNA).

The chemical reaction site is the site at which the particular compound is synthesized dictated by the order of V region sequences of the nucleic acid tag. An exemplary chemical reaction site is a primary amine. Many different types of chemical reaction sites in addition to primary amines can be introduced at any site, including the 3' terminus, the 5' terminus, or any other position on the nucleic acid tag. Exemplary chemical reaction sites include, but are not limited to, chemical components capable of forming amide, ester, urea, urethane, carbon-carbonyl bonds, carbon-nitrogen bonds, carbon-carbon single bonds, olefin bonds, thioether bonds, and disulfide bonds. In the case of enzymatic synthesis, co-factors may be supplied as are required for effective catalysis. Such co-factors are known to those of skill in the art. An exemplary cofactor is the phosphopantetheinyl group useful for polyketide synthesis.

An entire compound library is synthesized by carrying out alternate rounds of DNA-templated library splitting and chemical and/or biochemical coupling to each subsets of nucleic acid tags.

The plurality of chemical compounds produced are linked to nucleic acid sequence tags which facilitate identification of the chemical structure. Conventional DNA sequencing methods are readily available and useful for a determination of the sequence of the synthesis-directing nucleic acid tags. (See, e.g., Maniatis et al., eds., "Molecular Cloning: A Laboratory Manual", Second Edition, Cold Spring Harbor, N.Y. (1989)).

The compound library may be screened for a desired activity, for example the ability to catalyze a particular reaction or to bind with high affinity to an immobilized receptor. In most cases, the subpopulation of molecules with the desired activity, as well as their nucleic acid tags, are physically partitioned away from siblings during the selection. Following selection, the nucleic acid tags attached to the selected molecules are synthesized by the polymerase chain reaction ("PCR") (Saiki et al., *Science* (1988) 239 (4839) 487-491). The 5'hydroxyl of the 5'-end primer used to synthesize the coding strand is modified with a phosphate group tethered to a fresh primary amine chemical reaction site. After synthesis, the coding strand is separated from the non-coding strand. Because the nucleic acid tags direct the library synthesis, rather than merely reporting on the synthetic history of individual compounds, the coding strands amplified from the first library can be used to direct the construction of a second generation compound library. Iteration of this procedure, by carrying out multiple rounds of selection, DNA tag amplification, and library resynthesis, allows individual desirable compounds to be amplified from extremely complex libraries.

An entire compound library or individual library members produced by the above may be evaluated for one or more desired activities in screening assays capable of distinguishing compounds which modulate an activity or possess a desired structural or functional property. Exemplary assays and functional analyses include, but are not limited to, enzymatic assays, non-enzymatic catalytic assays, protein-protein binding assays, receptor/ligand binding assays and cell-based assays. More specifically, exemplary cell-based methods are based on; (1) differential binding of library compounds to a cell surface (i.e., binding to cancer cell and not a non-cancer cell); (2) binding of library compounds to components of a cell extract (e.g., binding to a cell fraction produced by separating an entire cell extract on a sucrose gradient); (3) library compounds capable of endocytosis by a cell and (4) in vivo localization and binding properties of library compounds by injecting the library into an animal. (See, e.g., Arap et al., *Science* (1998) 279(5349) 377-80 which describes in vivo selection of phage display libraries to isolate peptides that home specifically to tumor blood vessels). As will be appreciated by those of skill in the art, such assays may be performed on entire libraries of compounds synthesized by the methods described herein or sub populations derived therefrom.

The number of possible recognition compounds for which ligands may be synthesized and identified by DPCC is virtually unlimited. Recognition compounds include, but are not limited to, oligonucleotides, single stranded RNA, single stranded DNA, DNA binding proteins, RNA binding proteins, peptide nucleic acids, peptides, depsipeptides, polypeptides, antibodies, peptoids, polymers, polysiloxanes, inorganic compounds of molecular weight greater that 50 daltons, organic compounds of molecular weight between about 3000 daltons and about 50 daltons or combinations thereof.

Desired ligands produced by the nucleic acid tag-directed combinatorial library methods include, but are not limited to, oligonucleotides, single stranded RNA, single stranded DNA, DNA binding proteins, RNA binding proteins, peptide nucleic acids, peptides, depsipeptides, polypeptides, antibodies, peptoids, polymers, polysiloxanes, inorganic compounds of molecular weight greater that 50 daltons, organic compounds of molecular weight between about 3000 daltons and about 50 daltons or combinations thereof.

In addition to allowing amplification of selected library members, the method permits evolution of the encoded compound libraries. More specifically, genetic recombination between the nucleic acid tags which encode selected subpopulations of compounds is carried out in vitro by mutagenesis or random fragmentation of the nucleic acid tag sequence, followed by the generation of related nucleic acid sequences ("gene shuffling", Stemmer, *Nature*, (1994) 370 389-391; Stemmer et al., U.S. Pat. No. 5,811,238) and subsequent step-wise synthesis of additional compounds. Iteration of this procedure, by carrying out multiple rounds of selection, DNA tag amplification, genetic recombination and library resynthesis, allows individual desirable compounds to evolve from extremely complex libraries.

In some embodiments, a unique restriction site is introduced into each specific hybridization sequence. By way of example, partial digestion of a library with 11 specific hybridization sequences is accomplished by partial digestion with 11 corresponding restriction enzymes, followed by a primerless PCR reassembly reaction, allowing the nucleic acid tags for compounds that have been selected out of the library to be recombined with one another and further synthetic steps carried out. By analogy to gene shuffling for protein synthesis (Crameri et al., Nature (1998) 391 288-291), the ability to carry out genetic recombination of compound libraries vastly increases the efficiency with which the diversity in the compound libraries can be explored and optimized. In some embodiments, the gene has been circularized Accordingly, polynucleotide shuffling yields a population of variant nucleic acid sequences, capable of directing the synthesis of structurally-related, and/or functionally-related molecules, and/or variants thereof to create ligands having one or more desired activities. For example, molecules capable of binding to the 5' untranslated region (UTR) of mRNA may be identified in this manner. In vitro amplification of a selected subpopulations of synthesis directing nucleic acid tags by PCR, either prior to or following "gene shuffling" is also possible using the methods described above.

In still another aspect, a device is provided. The device encompasses two arrays which include separate blocks. The block of the first array encompasses two or more addressable wells which include monoliths with attached recognition compounds which selectively bind ligands. The block of the second array encompasses two or more addressable wells which include ion exchange material. The wells which include monoliths with attached recognition compounds which selectively bind ligands are aligned with the wells including the ion exchange material. In some embodiments, the ion exchange material includes a monolith with ion exchange groups. In other embodiments, the ion exchange material includes a monolith with an anion exchange groups. Specific embodiments of any of the arrays described above may be used in the device reported herein.

As such, the above disclosure represents a novel device for performing DPCC (see e.g., Harbury et al., U.S. Patent Application No. US2006/0099626; Weisenger et al., PLoS ONE 7, e32299 for previous examples). As described above, a DNA library is translated into small molecules through repeated hybridization and chemistry cycles. The number of cycles depends upon the number of combinatorial chemistry steps that are required to make the library. Each synthon at a particular step will correspond to a unique codon. In the above embodiments, a hybridization array separates (i.e., route) the DNA library such that members of a DNA library (i.e., ligands) containing the same codon will be immobilized on one or more monoliths, which are attached to the cognate anti-codon recognition compound, into addressable wells. The hybridization array may be used in place of the splitting filters disclosed in Harbury et al., U.S. Patent Application No. US2006/0099626 or the sepharose columns described in Weissenger et al., PLoS ONE 7, e32299.

In another aspect, the hybridization array separates (i.e., route) the DNA library such that members of a DNA library (i.e., ligands) containing the same codon are immobilized on one or more monoliths, which are attached to the cognate anti-codon recognition compound, into addressable wells. A transfer array elutes the specifically hybridized members of the DNA library into separate addressable wells for further chemistry steps. Those of skill in the art will appreciate that use of such a device is not restricted to DNA libraries. Various diverse libraries of compounds can be routed in the same fashion with appropriately chosen recognition compounds and may be further processed as described below.

Figure 4:
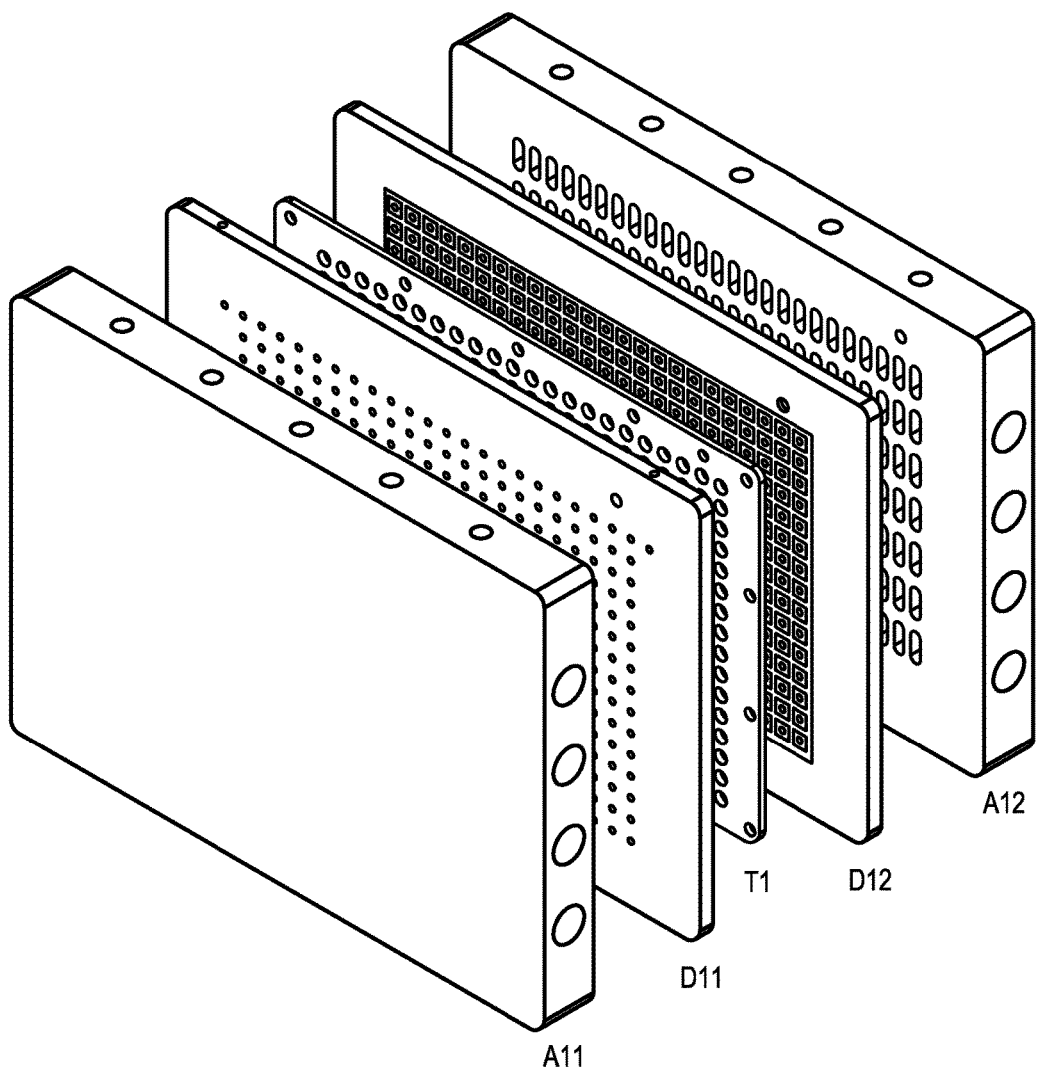
FIG. 4 illustrates an exemplary hybridization array with A12, D11, T1, D12 and A11 from left to right. Front face is on the top, and the top of the device is on the left.

An exemplary hybridization array is illustrated in FIG. 4 and includes five plates assembled from top to bottom: A12, D11, T1, D11 and A11. Plate T1 is an array where each addressable well contains a monolith with an attached specific anticodon recognition compound. Plates D11 and D12 are fabricated, for example, from a plastic containing holes that connect the monoliths with attached specific anticodon recognition compounds on plate T1 with the grooves on the inner faces of plates A11 and A12. The grooves are connected to channels through which air pressure and vacuum may be applied. Diaphragms placed between the A and D plates create a sealed continuous serpentine chamber consisting of the grooves on the A plates, the holes in the D plates, and the monoliths in the T plate. One of the D plates (D11) has ports through which liquid can enter and leave this chamber. The grooves in the top and bottom A plates are designed such that appropriate cyclical application of air pressure and vacuum to the channels in the A plates sets up a directional flow of the liquid in the serpentine chamber by, for example, a hybridization pump (see e.g., Weissenger et al., PLoS ONE 7, e32299). The net effect of the mesofluidic device may be likened to flowing the library of DNA ligands through an array of monolith columns attached to a specific anticodon recognition compound (i.e., the hybridization array), which are connected in series in a head-to-tail fashion. The skilled artisan will appreciate that N such devices may be connected in series so that a library can be partitioned, in principle, between an infinite number of hybridization array.

As the DNA library flows through the hybridization array, members of the DNA library containing the appropriate codon will hybridize to a monolith attached to a cognate anticodon recognition compound in the hybridization array. In some embodiments, cycling the DNA library through the device five times will ensure >90% partitioning of each codon (i.e., 90% of the DNA library with each codon is immobilized on the correct monolith with attached anticodon recognition compounds; the above requires that each pass of the DNA library through the monolith columns with attached anticodon recognition compounds partitions >40% of the cognate codon). Accordingly, at the end of this step, in some embodiments, >90% of the library will be immobilized on the hybridization array. In other embodiments, cycling the DNA library through the device five times will ensure between about 80% and about 90% partitioning of each codon Accordingly, at the end of this step, in some embodiments, between about 80% and about 90% of the library will be immobilized on the hybridization array at the end of this step. In some embodiments, the device is disassembled and the hybridization array that comprises monolith attached to a cognate anticodon recognition compound which have bound specific members of the DNA library (i.e., plate T1) are now used to form a transfer array.

Figure 5:
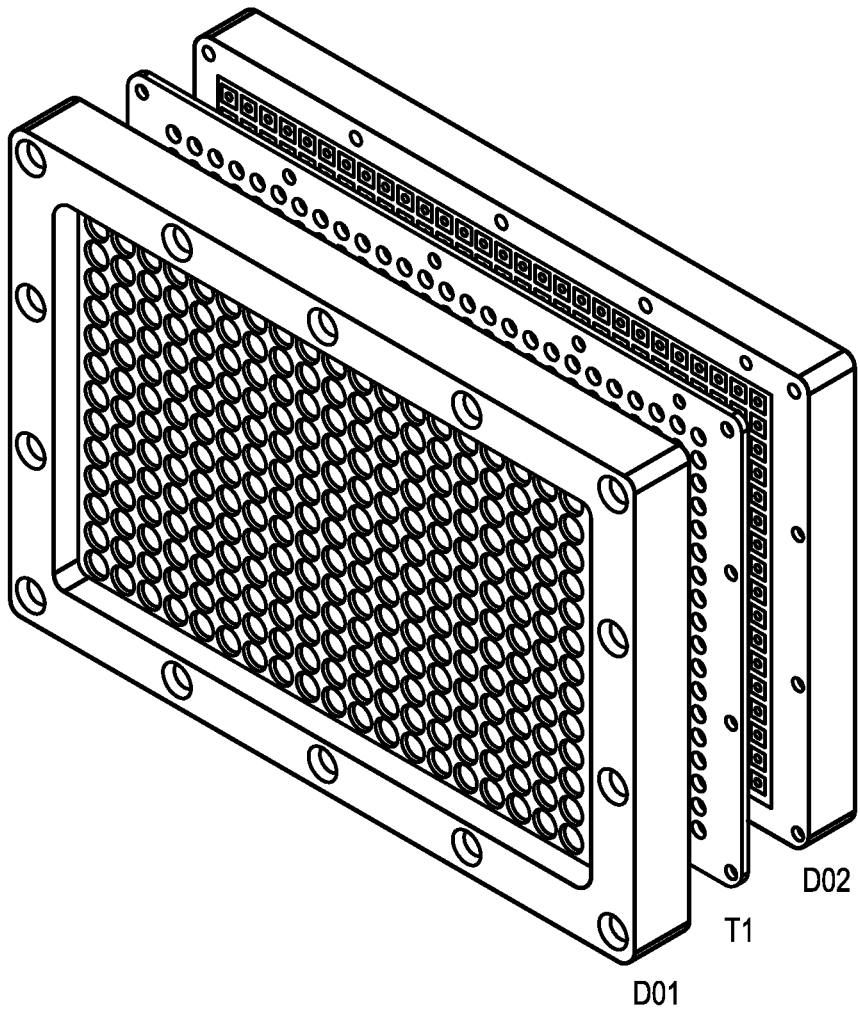
FIG. 5 illustrates an exemplary transfer array with D01, T1 and D02 from left to right. Front face is on the top, and the top of the device is on the left.

The transfer array allow parallel processing of the individual monolith columns in the array where the monoliths with attached anticodon recognition compounds have hybridized to specific members of the DNA library. In some embodiments, the transfer array includes plates D01, T1 and D02, as illustrated in FIG. 5. In some of these embodiments, silicone gaskets, are placed in the street pattern grooves on the inner face of plates D01 and D02 (face adjacent to T1) to prevent cross contamination of the addressable transfer array wells. Liquid applied to top of the D01 plate will be drawn through the assembly, for example, by centrifugation. The transfer array allows, washing, elution, and regeneration of the array with monoliths with attached anticodon recognition compounds. In some embodiments, the wells of the transfer array will contain ion exchange material which may be used to immobilize the specific members of the DNA library, which were hybridized to the monoliths with attached anticodon recognition compounds. In some embodiments, the address of the transfer array wells corresponds directly to the address of the hybridization array wells.

In addition, while the Figures illustrate the first routed codon towards the 3' end, the skilled artisan will appreciate that the first routed codon can also be routed to the 5' end. Those of skill in the art will also appreciate that more than one chemical step can follow each routing step.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety to disclose and describe the methods and/or materials in connection with which the publications are cited. It is understood that the present disclosure supersedes any disclosure of an incorporated publication to the extent there is a contradiction. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The following examples are provided for illustrative purposes only and are not intended to limit the scope of the invention.

EXAMPLES

Example 1: Titanium Silanization

Two #4 titanium grade 5 washers (United Titanium, outer diameter=0.3125 inch, inner diameter=0.125 inch, thickness=0.032 in) were threaded with a #6-32 tap (major diameter=0.136 inch, 32 threads/inch), washed with water, washed with acetone and then dried for 5 minutes. Each washer was then placed in an eppendorf tube and about 250 µl of a solution of 115 µl MPS ([3-(Methacryloyloxy)propyl]trimethoxysilane from Gelest) and 40 µl titanium n-butoxide (Gelest) dissolved in 345 µl heptane was then added, the tube shaken and turned upside down. After about 15 minutes, the washers were air-dried for 15-30 minutes, cured at 99° C. for 45 minutes, rinsed with acetone to remove excess unreacted reagents and air-dried for an additional 5 minutes.

Example 2: Monolith Formation and Bonding to Silanized Titanium

The silanized titanium washers were placed in a foil bag (Sigma #183385), the bag was flushed 5 times with $N_2$ and then closed. A mixture including 3 mL GMA, 1 mL EDMA, 3 mL 1-propanol, 2.4 mL 1,4-butanediol and 0.6 mL of water was sparged with $N_2$ for about 2 minutes, sonicated for about 10 minutes, at which time 10 mgs of AIBN (2,2'-azobis(2-methylpropionitrile) was added and the mixture was swirled to dissolve the initiator. The mixture was sonicated for an additional 1 minute, the head-space was purged with $N_2$ for about 30 sec, poured into the foil bag containing the silanized washers and sealed after removing any residual air/$N_2$. The washers were sandwiched between two outer aluminum plates, which ensured that the polymer only formed within the threaded holes ("wells") in the washers. The assembly was placed horizontally in the oven at 60° C. and incubated overnight. The plate/clamp assembly was removed from the oven, allowed to equilibrate to room temperature and dismantled to provide the monolith washers. Excess monolith was removed from the edges of the washer.

The monolith washer was placed in a filter-housing attached to a syringe and washed with 5 mL ethanol and 5 mL water.

Example 3: Silanization of Aluminum 6061 Array

A 3.125 mm thick aluminum plate of 6061 grade which had been machined to form a 384 well plate was washed with tap water, rinsed in distilled water for 5 minutes, washed in acetone for 15 minutes and air dried for 5 minutes. The plate was treated with 10% NaOH for about 10 minutes at about 45° C., blotted to remove excess NaOH and immersed in a 30% $HNO_3$ solution, until the entire surface of the plate was silver (1-3 minutes). The plate was then rinsed with distilled water, air dried for between about 10-60 minutes and treated with 30% MPS in acetone at 60° C. for 15 minutes, washed three times in acetone, air-dried and cured at 80° C. overnight. The plate was then washed with acetone and air-dried for about 10-15 minutes.

Example 4: Monolith Formation and Bonding to Silanized Aluminum 6061 Array

The silanized aluminum plate prepared in Example 3 was placed in a foil bag (Sigma #Z183393), the bag was flushed 5 times with $N_2$ and then closed. A mixture including 15 mL GMA, 5 mL EDMA, 15 mL 1-propanol, 12 mL 1,4-butanediol and 3 mL of water was sparged with $N_2$ for about 5 minutes, sonicated for about 10 minutes, at which time 25-50 mgs of AIBN was added and the mixture was swirled to dissolve the initiator. The mixture was sonicated for an additional 1 minute, the head-space was purged with $N_2$ for about 1 minute, poured into the foil bag containing the silanized aluminum plate and sealed after removing any residual air/$N_2$. The enclosed silanized aluminum plate was then sandwiched between two outer aluminum blocks which were secured with C-clamps. This ensured that the polymer only formed within the machined holes ("wells") in the plate. The assembly was placed horizontally in the oven at 60° C. and incubated overnight. The plate/clamp assembly was removed from the oven, allowed to equilibrate to room temperature and dismantled to provide the monolith array plate. Excess monolith was removed from the edges of the plate.

The monolith array was washed three times with between about 30 mL and about 40 mL of ethanol using vacuum (20 psi for between 10-60 seconds) to draw the ethanol through the monoliths attached to the aluminum plate. Then, between about 30 µl and about 40 µl of ethanol are added to each well and drawn through the monolith by application of vacuum (15-20 psi for between about 15 and about 20 seconds). Finally, between about 30 ul and about 40 µl of ethanol are added to each well and drawn through the monolith by a 1000 rpm spin for about 3 minutes. The monolith array was then washed with water in a similar manner. Ideally, every monolith in every well is permeable to solvent. A single impermeable well is enough to disqualify the array from further use.

Example 5: Azide Opening of Glycidyl Epoxide Monolith Attached to Aluminum 6061 Array Briefly, 20 µl of an aqueous solution of sodium azide (25 mmol in 8 mL of water and 4.6 mL of glacial acetic acid) was added to each well of the monolith array prepared in Example 4 and drawn through the monolith using vacuum. The above procedure was repeated once, the array was transferred to a bath containing the above azide solution, degassed for about five minutes, transferred to a reservoir filled with the above azide solution, incubated at 30° C. overnight, washed extensively with distilled water and stored in water to provide an azido alcohol functionalized monolith array.

Example 6: Attachment of an Oligonucleotide to Azido Functionalized Monolith Attached to Aluminum 6061 Array 30 ul of 'click' solution containing 0.1 M sodium phosphate, pH 7.0, 625 uM CuSO4, 3.125 mM THPTA (Tris(3-hydroxypropyltriazolylmethyl)amine, Sigma-Aldrich), 12.5 mM aminoguanidine-HCl, 0.3M NaCl, 12.5 mM ascorbate, and 1 nmol of the oligonucleotide to be immobilized (general structure 5'hexynl-TTTTTTTTTT-anticodon, purchased from Eurofins MWG Operon Inc., 2211 Seminole Drive Huntsville, Ala. 35805) was added to each azido-alcohol functionalized monolith in the array and incubated for a total of 1 hour. The 'click' solution was periodically (approximately, every 15 minutes) centrifuged out of the monolith, replenished with fresh ascorbate (addition of up to 3 ul of 100 mM ascotrbate), and added back to the same monolith. After 1 h incubation, the 'click' solution was centrifuged out of the monolith, and the array was washed three times with 30 ul of Tris-EDTA buffer (10 mM Tris-HCl, pH8.0, 1 mM EDTA) to chelate copper and quench the reaction. The resultant functionalized arrays were stored in 1 mM EDTA, 0.02% azide at 4° C.

The efficiency of click chemistry in attaching the 5'-hexynyl-oligo to the azide-modified monolith was assessed by removal of the oligo from the 'click' solution. Typically, the test reaction, consisting of equal concentrations of two oligos, a 5'-OH oligo (reference oligo) and the 5'-hexynyl oligo (test oligo), was incubated with the monolith in the 'click' buffer for a total of 1 hour at room temperature, after which it was centrifuged out of the monolith. The exhausted 'click' solution was analyzed by RP-HPLC on a C18 column with an acetonitrile gradient (mobile phase A: 135 mM triethylamine, 150 mM glacial acetic acid, 5% acetonitrile; mobile phase B: 25% mobile phase A, 75% acetonitrile) which separated the two oligos. The relative peak areas of the reference and the test oligos in the samples before and after incubation with the monolith were used to estimate the proportion of the 5'hexynyl-oligo that was 'clicked' onto the monolith.

Example 7: Propiolic Acid Blocking of Oligonucleotide Functionalized Monolith Attached to Aluminum 6061 Array Any unreacted azide groups in the monolith array treated as in example 6 were blocked by reacting with propiolic acid as follows. 30 ul of 'click' solution contained 0.1M sodium phosphate, pH 7.0, 625 uM CuSO4, 3.125 mM THPTA (Tris(3-hydroxypropyltriazolylmethyl)amine, Sigma-Aldrich), 12.5 mM aminoguanidine-HCl, 0.3 M NaCl, 12.5 mM ascorbate, and 8 mM propiolic acid was added to each functionalized monolith in the array and incubated for a total of 30 minutes. The 'click' solution was periodically (approximately every 15 min) centrifuged out of the monolith, replenished with fresh ascorbate (addition of up to 3 ul of 100 mM ascorbate), and added back to the same monolith. After 30 minutes incubation, the 'click' solution was centrifuged out of the monolith, and the array was washed three times with 30 ul of Tris-EDTA buffer (10 mM Tris-HCl, pH8.0, 1 mM EDTA) to chelate copper and quench the reaction. The treated arrays were stored in 1 mM EDTA, 0.02% azide at 4° C.

Example 8: Silanization of Aluminum 5038 Array

Silanization was performed as in Example 3, except the plate was treated with about 10% NaOH for about 15 minutes at about 45° C.

Example 9: Monolith Formation and Bonding to Silanized Aluminum 5038 Array

The procedure of Example 5 was used to provide the above monolith array.

Example 10: UV Treatment of Peek Washers

The washers were threaded using #10-32 tap (major diameter=0.19 inch, threads/inch=32) and submerged in a 1:10 EDMA:methanol solution in a scintillation vial. Each washer had a stainless steel cone at its center to disperse incident UV light. Also, cones were placed around the side of the washer to use the outer diameter face as a test for bonding strength. The vials were then immersed in the EDMA:methanol solution to a height of about 1 cm. The washers were then irradiated with 302 nm UV light for 15 minutes from a distance of about 3 cm, flipped and irradiated again with 302 nm UV light for 15 minutes from a distance of about 3 cm, rinsed 3× with methanol, air dried and stored in a foil bag under nitrogen. The washers were used to cast monoliths according to the procedure described in Example 2.

What is claimed is:

1. A device for preparative partitioning of a nucleic acid library, comprising:
   a plurality of hybridization affinity monolith columns arrayed within a solid block,
   wherein each monolith column is functionalized with covalently bound oligonucleotides at a density of between about 1 pmol/10 µL and about 1 µmol/10 µL, and
   wherein each monolith column is positioned within a hole extending through the block.

2. The preparative partitioning device of claim 1, wherein each monolith column is sufficiently bound to the inner wall of the through hole to remain fixed to the block during forced convective flow through the monolith column.

3. The preparative partitioning device of claim 2, wherein each monolith column is bound sufficiently to remain fixed to the block during convective fluid flow forced through the monolith column at a pressure of 20 PSI.

4. The preparative partitioning device of claim 1, wherein the block is composed of material capable of maintaining the monolith columns in addressable alignment during forced convective flow through the monolith columns and dissociation and transfer of the partitioned subpopulations of nucleic acid molecules from the monolith columns.

5. The preparative partitioning device of claim 4, wherein the block is composed of metal.

6. The preparative partitioning device of claim 5, wherein the metal is aluminum.

7. The preparative partitioning device of claim 6, wherein the surface of the aluminum is silanized.

8. The preparative partitioning device of claim 7, wherein the monolith column is an organic polymer monolith column and the covalent bonds between monolith column and surface-silanized aluminum are carbon-carbon bonds.

9. The preparative partitioning device of claim 1, wherein the monolith column is an organic polymer monolith column.

10. The preparative partitioning device of claim 9, wherein the monolith column is poly(GMA-co-EDMA).

11. The preparative partitioning device of claim 1, wherein each monolith column is capable of binding between about 0.5 fmol/μL and between about 0.4 nmol/μL of library nucleic acid.

12. The preparative partitioning device of claim 1, wherein the rate constant of binding of library nucleic acid molecules to monolith column oligonucleotides having respectively complementary sequence is on average between about $1\times10^3$ $M^{-1}s^{-1}$ and about $1\times10^6 M^{-1}s^{-1}$.

13. A device for preparative partitioning of a nucleic acid library, comprising:
a plurality of hybridization affinity monolith columns arrayed within a solid block,
wherein each monolith column is functionalized with covalently bound oligonucleotides at a density of between about 1 pmol/10 μL and about 1 μmol/10 μL, and
wherein each monolith column is positioned within a hole extending through the block and comprises means for remaining fixed in said hole during forced convective flow therethrough.

14. The preparative partitioning device of claim 13, comprising means for maintaining the monolith columns in addressable alignment during forced convective flow through the monolith columns and dissociation and transfer of the partitioned subpopulations of nucleic acid molecules from the monolith columns.

15. The device of claim 1, wherein said covalently bound oligonucleotides are of a single hybridization binding specificity for each monolith column.

16. The device of claim 1, wherein each of the plurality of hybridization affinity monolith columns is functionalized with oligonucleotides of unique hybridization binding specificity.

17. A device for preparative partitioning of a nucleic acid library, comprising:
a plurality of hybridization affinity monolith columns fluidly connected in series,
wherein each hybridization affinity monolith column is functionalized with covalently bound oligonucleotides at a density of about 1 pmol/10 μL to about 1 μmol/10 μL.

18. The device of claim 17, wherein said covalently bound oligonucleotides are of a single hybridization binding specificity for each monolith column.

19. The device of claim 17, wherein each of the plurality of hybridization affinity monolith columns is functionalized with oligonucleotides of unique hybridization binding specificity.

20. The device of claim 17, wherein the plurality of hybridization affinity monolith columns are arrayed within a solid block.

21. The device of claim 20, wherein each of the plurality of hybridization affinity monolith columns is separately positioned within and bound to the inner wall of a hole extending through the block.

22. The device of claim 21, wherein the block is metal.

23. The device of claim 22, wherein the block is silanized aluminum and each hybridization affinity monolith column is covalently bound to the inner wall of the hole.

24. A device for preparative partitioning of a nucleic acid library, comprising:
a plurality of hybridization affinity monolith columns fluidly connected in series,
wherein each hybridization affinity monolith column is functionalized with covalently bound oligonucleotides at a density of about 1 pmol/10 μL to about 1 μmol/10 μL, and
means for maintaining the plurality of hybridization affinity monolith columns in arrayed alignment during preparative partitioning of a nucleic acid library.

* * * * *